US012617812B2

(12) United States Patent
Zhu et al.

(10) Patent No.: US 12,617,812 B2
(45) Date of Patent: May 5, 2026

(54) PLATINUM(IV) COMPLEXES, METHODS OF MANUFACTURE, COMPOSITIONS CONTAINING, AND METHODS OF USE THEREOF

(71) Applicant: City University of Hong Kong, Kowloon (HK)

(72) Inventors: Guangyu Zhu, Pok Fu Lam (HK); Zhiqin Deng, Xichang (CN)

(73) Assignee: City University of Hong Kong, Kowloon (HK)

( * ) Notice: Subject to any disclaimer, the term of this patent is extended or adjusted under 35 U.S.C. 154(b) by 920 days.

(21) Appl. No.: 17/824,174

(22) Filed: May 25, 2022

(65) Prior Publication Data

US 2023/0024341 A1 Jan. 26, 2023

Related U.S. Application Data

(60) Provisional application No. 63/215,401, filed on Jun. 25, 2021.

(51) Int. Cl.
*C07F 15/00* (2006.01)
*A61K 31/555* (2006.01)
(Continued)

(52) U.S. Cl.
CPC ........ *C07F 15/0093* (2013.01); *A61K 31/555* (2013.01); *A61K 41/0057* (2013.01);
(Continued)

(58) Field of Classification Search
CPC .............. C07F 15/0093; A61K 31/555; A61K 41/0057; A61N 5/062; A61N 2005/0659; A61P 31/04; A61P 35/00
See application file for complete search history.

(56) References Cited

U.S. PATENT DOCUMENTS 10,899,781 B2 1/2021 Zhu et al.
2019/0276486 A1* 9/2019 Zhu ..................... C07F 15/0093

FOREIGN PATENT DOCUMENTS

CN 105622674 6/2016
CN 105622674 A * 6/2016 .......... C07F 15/0093
(Continued)

OTHER PUBLICATIONS

Oberoi, H. S. et al. Nanocarriers for delivery of platinum anticancer drugs. Adv. Drug Deliv. Rev. 2013, 65, 1667-1685. (Year: 2013).*
(Continued)

*Primary Examiner* — Jeffrey H Murray
*Assistant Examiner* — Kristen W Romero
(74) *Attorney, Agent, or Firm* — Renner, Kenner, Greive, Bobak, Taylor & Weber

(57) ABSTRACT

A platinum(IV) complex selected from the group consisting of

Formula II(a)

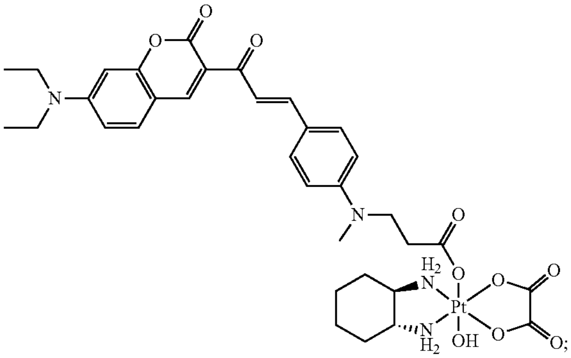

;

Formula II(b)

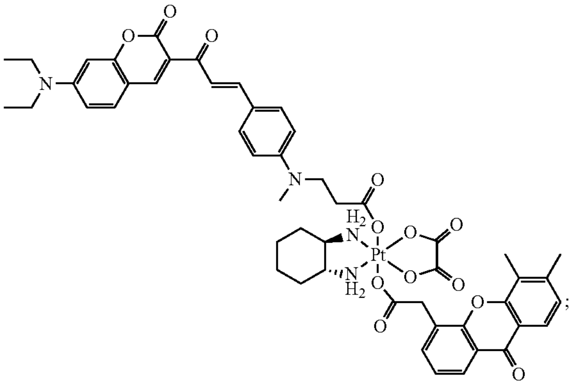

;

Formula II(c)

; and (Continued)

-continued

Formula II(d)

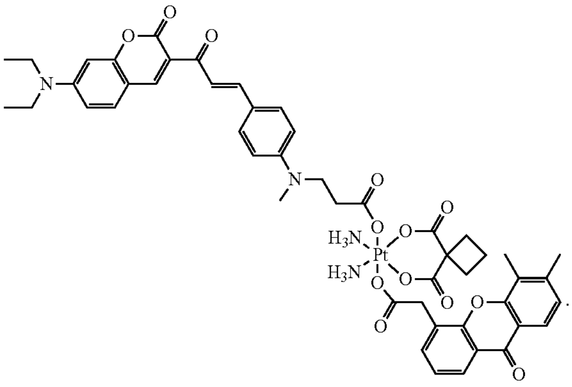

Various methods contain steps for manufacturing the platinum(IV) complexes, and a pharmaceutical composition contains the platinum(IV) complex are also addressed.

7 Claims, 16 Drawing Sheets

(51) Int. Cl.

| | |
|---|---|
| ***A61K 41/00*** | (2020.01) |
| ***A61N 5/06*** | (2006.01) |
| ***A61P 31/04*** | (2006.01) |
| ***A61P 35/00*** | (2006.01) |

(52) U.S. Cl.

CPC .............. *A61N 5/062* (2013.01); *A61P 31/04* (2018.01); *A61P 35/00* (2018.01); *A61N 2005/0659* (2013.01)

(56) References Cited

FOREIGN PATENT DOCUMENTS

| | | |
|---|---|---|
| CN | 110423254 | 11/2019 |
| CN | 114539320 | 5/2022 |

OTHER PUBLICATIONS

Mügge, C. et al. Structure, solution chemistry, antiproliferative actions and protein binding properties of non-conventional platinum(II) compounds with sulfur and phosphorus donors. Dalton Trans. 2011, 40, 2006-2016. (Year: 2011).*

Zou, Q. et al. Synthesis and in Vitro Photocytotoxicity of Coumarin Derivatives for One- and Two-Photon Excited Photodynamic Therapy. J. Med. Chem. 2013, 56, 5288-5294. (Year: 2013).*

Deng, Z. et al. A Photocaged, Water-Oxidizing, and Nucleolus-Targeted Pt(IV) Complex with a Distinct Anticancer Mechanism. J. Am. Chem. Soc. 2020, 142, 7803-7812.; published Mar. 27, 2020. (Year: 2020).*

Cancer treatment; Mayo Clinic. https://www.mayoclinic.org/tests-procedures/cancer-treatment/about/pac-20393344. Last accessed: Dec. 11, 2025. Earliest publication date: Mar. 13, 2020. (Year: 2020).*

Diseases and Conditions: What's the difference between a bacterial infection and a viral infection? Mayo Clinic. https://www.mayoclinic.org/diseases-conditions/infectious-diseases/expert-answers/infectious-disease/faq-20058098. Last accessed: Dec. 11, 2025. Earliest publication date: Jan. 19, 2014. (Year: 2014).*

Infection. NCI Dictionary of Cancer Terms. https://www.cancer.gov/publications/dictionaries/cancer-terms/def/infection. Last accessed: Dec. 11, 2025. Earliest publication date: Apr. 23, 2018. (Year: 2018).*

Definition of "subject." Oxford Dictionary. Last accessed: Dec. 11, 2025. (Year: 2025).*

Z. Wang et al; Phorbiplatin, a Highly Potent Pt(IV) Antitumor Prodrug That Can be Controllably Activated by Red Light; Chem 5, 3151-3165, Dec. 12, 2019; p. 3150-3165.

Z. Deng et al; An intramolecular photoswitch can significantly promote photoactivation of Pt(IV) prodrugs; Chem. Sci., 2021, 12, 6536-6542.

Zhiqin Deng et al., Near-infrared-activated anticancer platinum(IV) complexes directly photooxidize biomolecules in an oxygen-independent manner; Nature Chemistry, 2023; 15 (7): 930, DOI: 10.1038/s41557-023-01242-w.

China NIPA Office Action from related filing CN 202210706159 dated Mar. 13, 2026.

* cited by examiner

Compoud 1
Compoud 2
Compoud 1
Compoud 2
Ligand 3
Ligand 3
Complex 4
Ligand 3
Complex 5

Complex 4
DMXAA
Complex 6
Complex 5
DMXAA
Complex 7

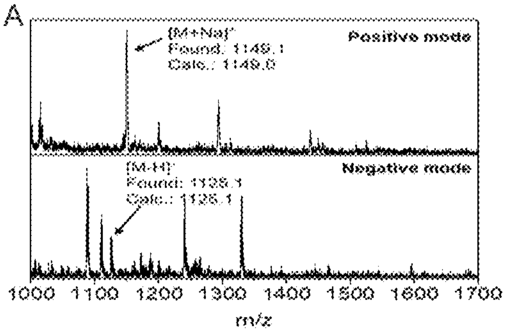
Fig. 23A
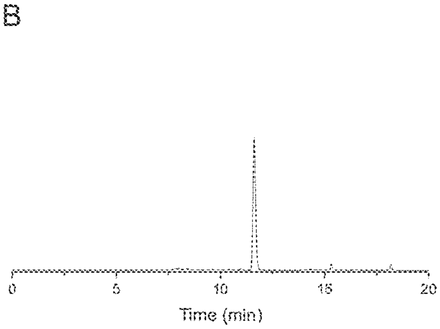
Fig. 23B
Fig. 24A
Fig. 24B
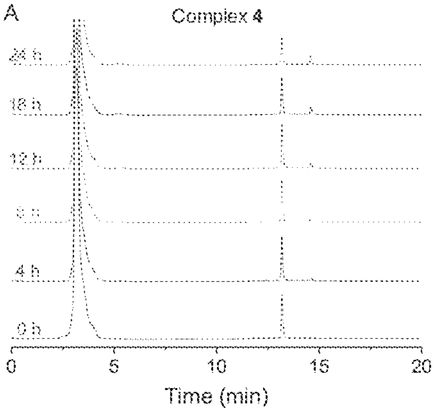
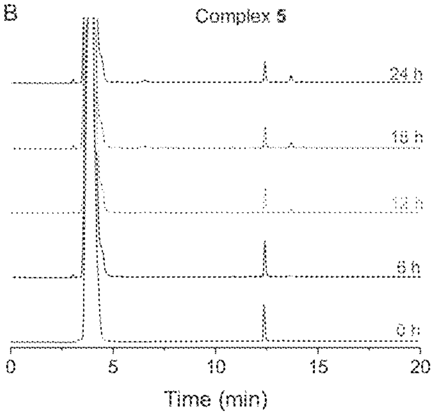
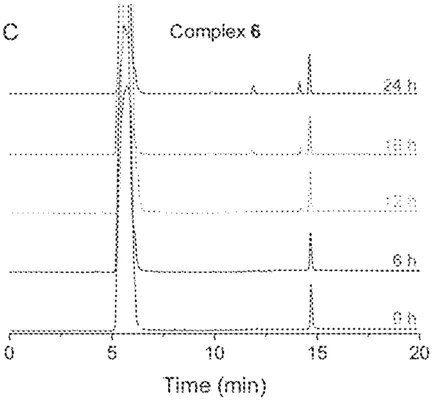
Fig. 24C
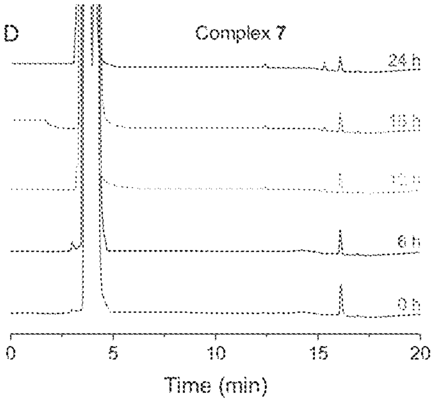
Fig. 24D Fig. 25A
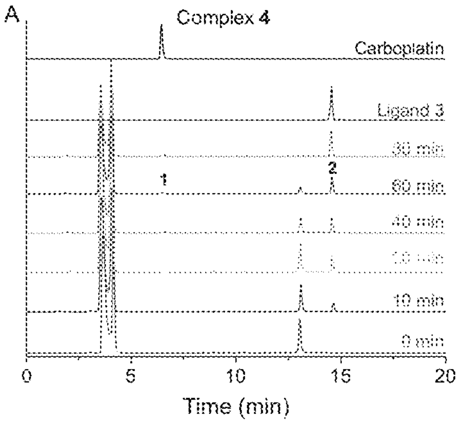
Fig. 25B
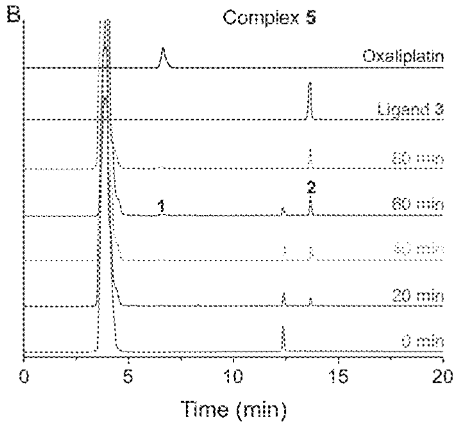
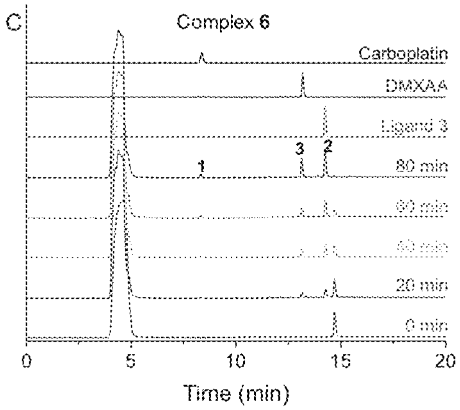
Fig. 25C
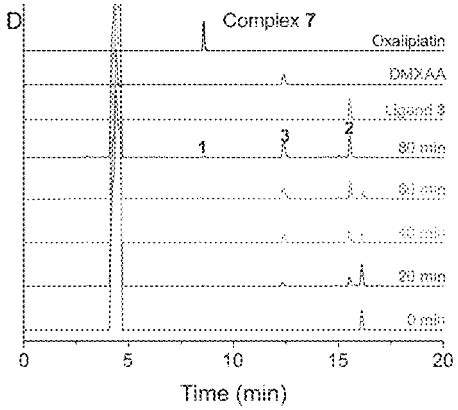
Fig. 25D Fig. 26A
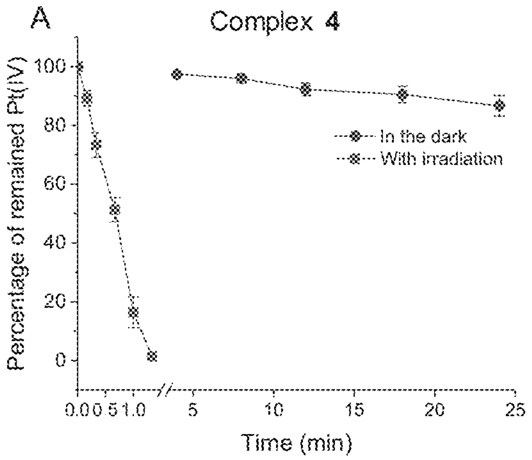
Fig. 26B
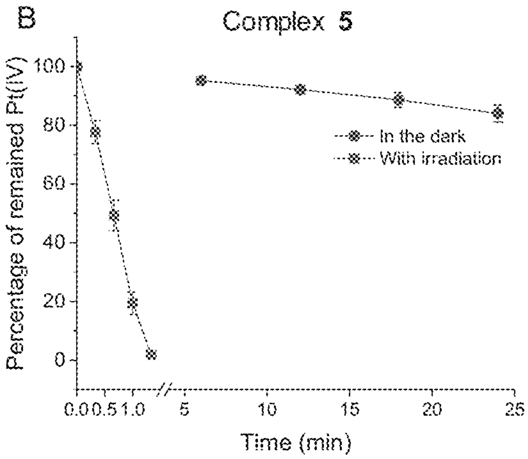
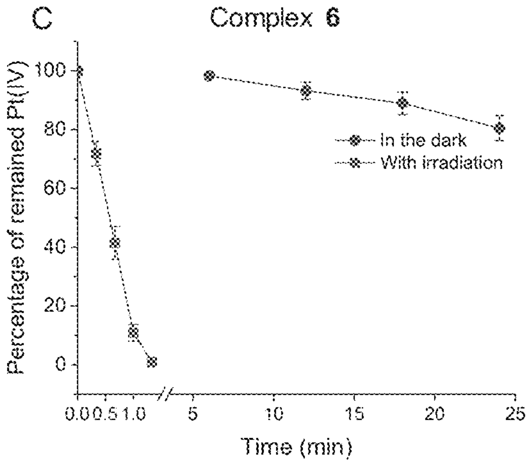
Fig. 26C
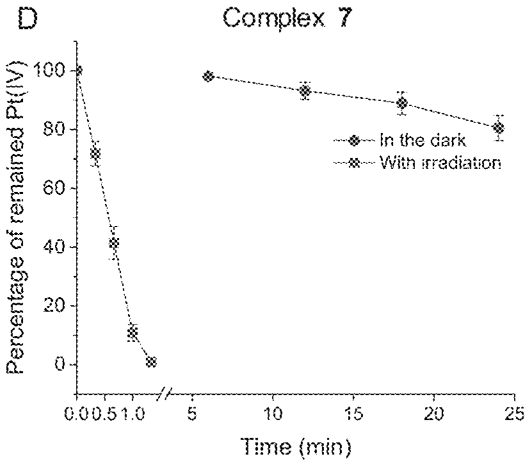
Fig. 26D Fig. 27A
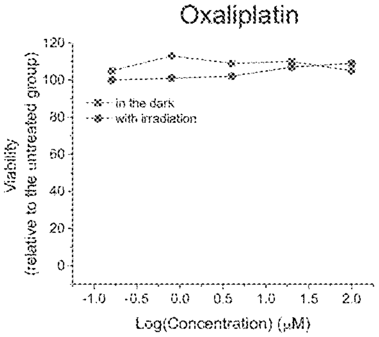
Fig. 27B
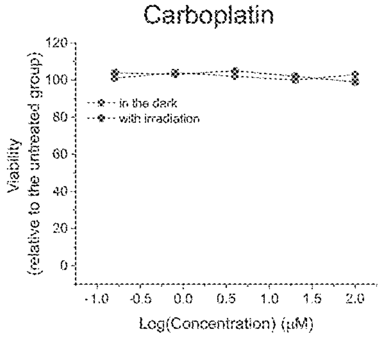
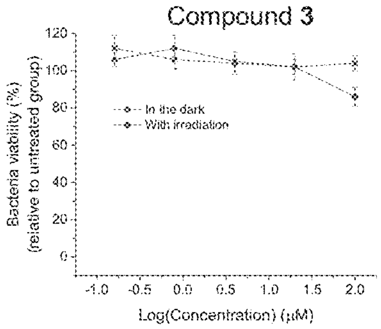
Fig. 27C
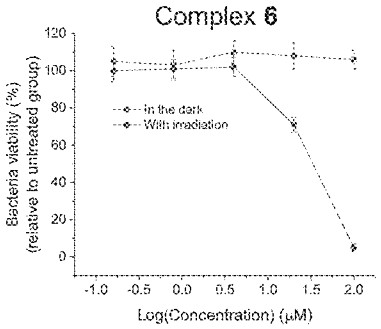
Fig. 27D
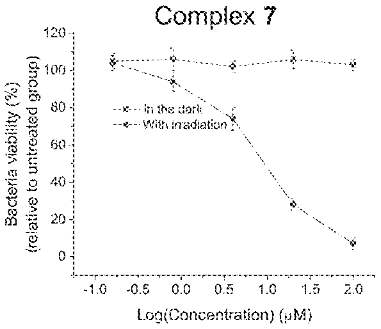
Fig. 27E Fig. 28A
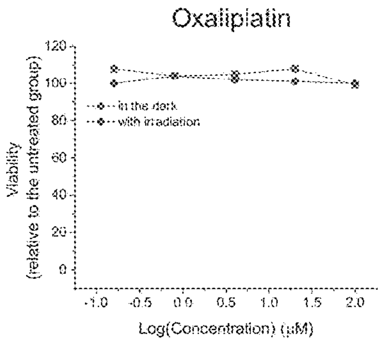
Fig. 28B
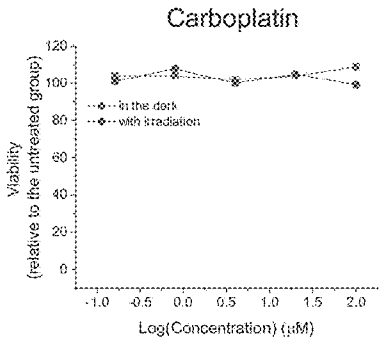
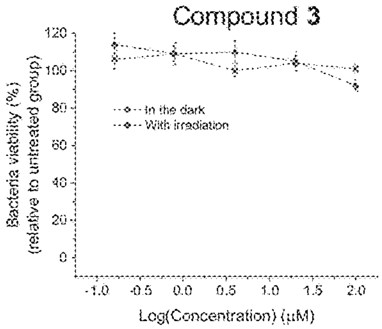
Fig. 28C
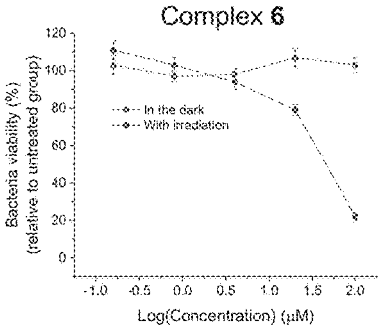
Fig. 28D
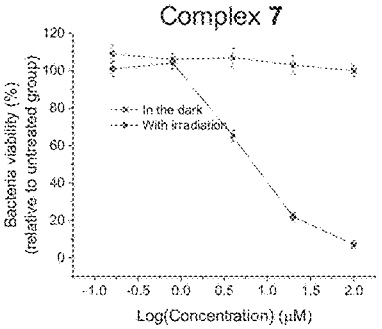
Fig. 28E

PLATINUM(IV) COMPLEXES, METHODS OF MANUFACTURE, COMPOSITIONS CONTAINING, AND METHODS OF USE THEREOF

FIELD OF THE INVENTION

The present invention elates to platinum-based anti-cancer, anti-tumor, and anti-infection drugs. More specifically, the present invention relates to platinum-based anti-cancer chemotherapy drugs and anti-infection drugs.

BACKGROUND

Platinum-based anticancer drugs are the most widely used chemotherapy agents in current clinical practice. It is estimated that more than 50% of cancer patients receiving chemotherapy are treated with platinum drugs alone or in combination with other anticancer drugs. The therapeutic outcome of platinum drugs, however, is often limited by the serious side effects and drug resistance of cancer cells. For example, current chemotherapeutic agents may be activated in non-pathological tissue.

While certain specific cytotoxic platinum complexes are also known for medical use (see, for example, US 2018/155382 A1, to Zhu, et. al., assigned to City University of Hong Kong, published on Jun. 7, 2018, the entirety of which is incorporated herein by reference), additional complexes are desirable.

Some previous platinum anticancer complexes bind to the DNA of cancer cells and induce DNA damage to kill cancer cells. However, the therapeutic efficiency of these drugs is limited by factors such as low platinum-DNA binding efficiency, poor selectivity between cancer and normal cells, the resistance of cancer cells towards drugs (e.g., enhanced DNA repair ability), etc.

Ultraviolet (UV) and visible light photo-activated drugs (herein including pro-drugs) are known and have shown activity against, for example, cancerous tumors. However, use of current photosensitizers in such photo-activated drugs suffers from significant problems, such as side-effects, phototoxicity and cytotoxicity in non-targeted tissue, drug resistance, oxygen-dependent reactions, the requirement that the cancer/tumor/infection to be close to the skin surface and/or other internal body cavity areas accessible to UV/visible light sources, etc. which may severely limit their use and/or effectiveness.

It is known that bacteria can quickly develop and transfer drug resistance to conventional antibiotics. Furthermore, conventional antibacterial photodynamic therapy (APDT) agents strongly rely on intracellular drug accumulation for their antibacterial effects. Therefore, the bacterial cell wall and membrane are present significant barriers to the successful application of APDT and related drugs.

Accordingly, given the current inherent limitations to current technologies, there remains a need to develop additional platinum therapies and drugs for the treatment of cancer, tumors and/or infections that can overcome these limitations. Furthermore, there is a great need to develop anticancer and antibacterial agents with both controllable activation properties as well as tumor-specific targeting. The need further exists for platinum complexes that may effectively overcome drug resistance through a distinct and controllable mechanism of action. The need further exists for photoactivatable complexes that may transform to strong oxidants to oxidize survival-related intracellular biomolecules and generate reactive oxygen species (ROS), lipid peroxide, etc. to disrupt intracellular redox balance to kill cancer cells or bacteria.

SUMMARY OF THE INVENTION

An embodiment of the present invention relates to a platinum(IV) complex of Formula I:

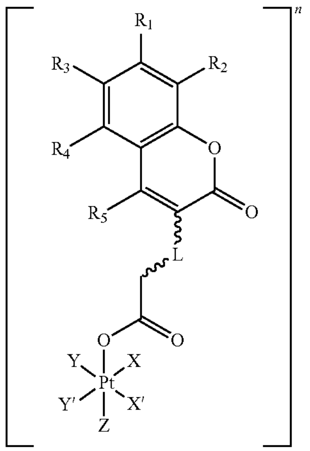

where X, X', Y, Y', and Z are each independently an electron donor ligand, $R_1$~$R_5$ are each independently a functional group, L is the linker unit, and n is selected from the group of 0, a positive charge, and a negative charge.

An embodiment of the present invention relates to various methods for manufacturing embodiments of the platinum (IV) complex herein. An embodiment of the present invention relates to a method of treating cancer, a tumor, or an infection in a subject comprising the steps of administering to the subject an effective dose of the platinum(IV) complex herein, and administering to the subject near-infrared radiation (NIR). An embodiment of the present invention relates to a pharmaceutical composition containing the platinum (IV) complex described herein.

Without intending to be limited by theory, it is believed that the present invention may provide one or more benefits such as, new and improved photo-oxidants and photo-oxidation; improved treatment for cancer, tumors and/or infections; reduced patient toxicity; improved therapy targeting; decreased phototoxicity as compared to UV treatments; enhanced anticancer and antibacterial treatments and compositions; controllable temporal and location-specific activation; reduced side effects, platinum complexes that overcome cisplatin resistance, platinum resistance, PDT resistance, etc.; and methods to disrupt intracellular redox balance to kill cancer cells or bacteria.

BRIEF DESCRIPTION OF THE DRAWINGS

FIG. 23A shows an ESI-MS analysis of complex 7;

FIG. 23B shows an HPLC chromatograph of complex 7;

FIG. 24A shows a RP-HPLC (254 nm) chromatogram of complex 4;

FIG. 24B shows a RP-HPLC (254 nm) chromatogram of complex 5;

FIG. 24C shows a RP-HPLC (254 nm) chromatogram of complex 6;

FIG. 24D shows a RP-HPLC (254 nm) chromatogram of complex 7;

FIG. 25A shows a RP-HPLC (254 nm) chromatograms of complex 4;

FIG. 25B shows a RP-HPLC (254 nm) chromatograms of complex 5;

FIG. 25C shows a RP-HPLC (254 nm) chromatograms of complex 6;

FIG. 25D shows a RP-HPLC (254 nm) chromatograms of complex 7;

FIG. 26A shows the percentage of complex 4 remaining after irradiation and without irradiation;

FIG. 26B shows the percentage of complex 5 (10 μM) remaining after irradiation and without irradiation;

FIG. 26C shows the percentage of complex 6 (10 μM) remaining after irradiation and without irradiation;

FIG. 26D shows the percentage of complex 7 (10 μM) remaining after irradiation and without irradiation;

FIG. 27A shows the viability of *Escherichia coli* (DH5-α) after treatment of Oxaliplatin after irradiation and without irradiation;

FIG. 27B shows the viability of *Escherichia coli* (DH5-α) after treatment of Carboplatin after irradiation and without irradiation;

FIG. 27C shows the viability of *Escherichia coli* (DH5-α) after treatment of compound 3 after irradiation and without irradiation;

FIG. 27D shows the viability of *Escherichia coli* (DH5-α) after treatment of complex 6 after irradiation and without irradiation;

FIG. 27E shows the viability of *Escherichia coli* (DH5-α) after treatment of complex 7 after irradiation and without irradiation;

FIG. 28A shows the viability of *Staphylococcus aureus* after treatment of Oxaliplatin after irradiation and without irradiation;

FIG. 28B shows the viability of *Staphylococcus aureus* after treatment of Carboplatin after irradiation and without irradiation;

FIG. 28C shows the viability of *Staphylococcus aureus* after treatment of compound 3 after irradiation and without irradiation;

FIG. 28D shows the viability of *Staphylococcus aureus* after treatment of complex 6 after irradiation and without irradiation; and FIG. 28E shows the viability of *Staphylococcus aureus* after treatment of complex 7 after irradiation and without irradiation.

Figure 1:
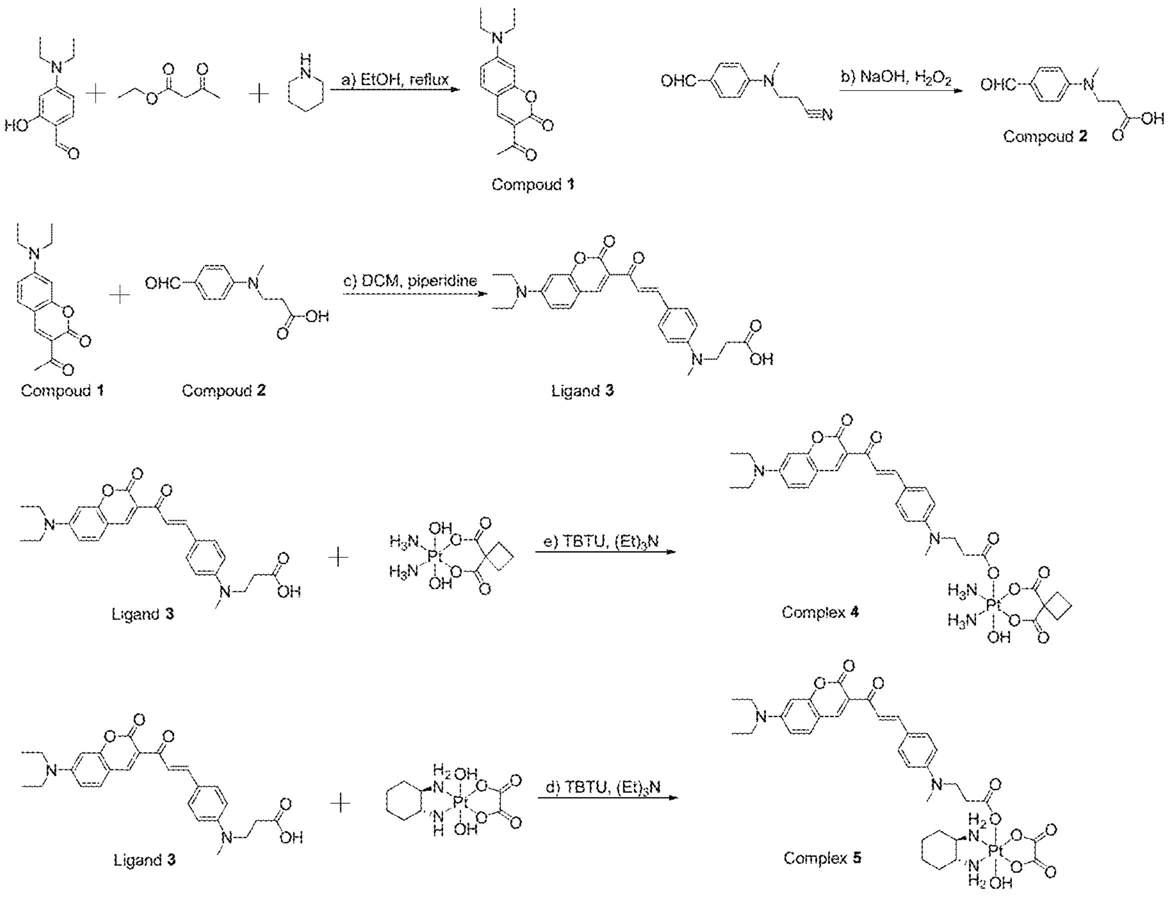
FIG. 1 shows an embodiment of synthesis steps for complex 4 (i.e., Formula II(c)) and complex 5 (i.e., Formula II(a))

The figures herein are for illustrative purposes only and are not necessarily drawn to scale.

DESCRIPTION OF THE PREFERRED EMBODIMENTS

Unless otherwise specifically noted, all reactions are carried out in the dark. All the reagents and solvents are used as received without further purification. NMR data is recorded with a Bruker AVANCE III 400 MHz spectrometer or a Bruker Ascend AVANCE III 600 MHz spectrometer at room temperature. ESI-MS data is recorded with a Liquid Chromatograph-Mass Spectrometer (API-3200 Triple-Q MS/MS). Analytical HPLC (RPLC) is conducted on a Shimadzu Prominence LC-20AT HPLC system, with a reversed-phase C18 column (Phenomenex Garmin 250×4.60 mm, 5 m, 110 Å). The photometric diode array (PDA) detector is applied to scan the absorption spectrum from 190-800 nm. Solvent A ($H_2O$ with 5% acetonitrile (ACN) and 0.01% trifluoroacetic acid (TFA)) and solvent B (ACN (what %?) with 5% $H_2O$ and 0.01% TFA by volume) is used for a gradient elution at a flow rate of 1.2 mL/min. The samples are eluted as follows: 100% $H_2O$ (0 min)—50% $H_2O$+50% ACN (5 min)—50% $H_2O$+50% ACN (7 min)—100% ACN (10 min)—100% ACN (13 min)—100% $H_2O$ (15 min) all by volume. Platinum content is measured by an Inductively Coupled Plasma-Optical Emission Spectrometer (ICP-OES) (PE Optima 8000).

Unless otherwise specifically provided, all tests herein are conducted at standard conditions which include a room and testing temperature of 25° C., sea level (1 atm.) pressure, pH 7 and all measurements are made in metric units. Furthermore, all percentages, ratios, etc. herein are by weight, unless specifically indicated otherwise. It is understood that unless otherwise specifically noted, the materials compounds, chemicals, etc. described herein are typically commodity items and/or industry-standard items available from a variety of suppliers worldwide.

As used herein, the term "anticancer agent" means a chemical compound that may kill cancer cells with or without a certain activation method.

As used herein, the term "NIR" and "NIR-light" indicate near-infrared radiation and near-infrared light, respectively, such as that having a wavelength of from about 700 nanometers (nm) to about 1400 nm; or from about 800 nm to about 1100 nm; or from about 800 nm to 1000 nm.

As used herein the term "photodynamic therapeutic agent" means a compound that is non-toxic or of low-toxicity towards cancer/tumor cells before light activation via irradiation; however, upon irradiation with light; or a certain wavelength light, it may directly or indirectly kill the cancer/tumor cells.

As used herein, the term "photo-oxidant" means a compound that is non-toxic and of low reduction potential before light activation via irradiation; however, upon irradiation with light; or a certain wavelength light, it will transform to an oxidant which possesses high reduction potential and may oxidize biomolecules to kill, for example, cancer cells.

As used herein, the term "platinum drug-resistant" means cells, such as bacteria, cancer cells, tumor cells, etc., which are resistant to clinical platinum drugs by themselves, and exclude the platinum(IV) complexes described herein.

As used herein, the term "prodrug" means a compound possessing little drug activity itself, but which may be converted, typically in vivo, into a compound possessing significantly greater pharmacological activity.

An embodiment of the present invention relates to a platinum(IV) complex according to Formula I:

Formula I

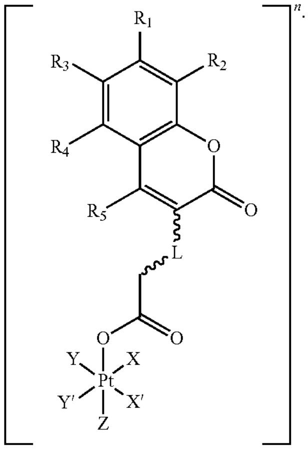

In Formula I, X, X', Y, Y', and Z connected directly to the platinum atom. X, X', Y, Y', Z and the platinum atom are together referred to herein as the "platinum portion". X, X', Y, Y', and Z are each independently an electron donor ligand; or X, X', Y, and Y' are each independently an electron donor ligand selected from the group consisting of a nitrogen-containing unidentate, bidentate, or tridentate ligand, an oxygen-containing unidentate or bidentate ligand, a phosphorous-containing unidentate or bidentate ligand, a sulfur-containing unidentate or bidentate ligand, a halogen-containing unidentate or bidentate ligand and a combination thereof; or an oxygen-containing bidentate ligand, a sulfur-containing unidentate or bidentate ligand, a nitrogen-containing unidentate or bidentate ligand, a phosphorous-containing unidentate or bidentate ligand and a combination thereof; or an oxygen-containing bidentate ligand, a nitrogen-containing unidentate or bidentate ligand and a combination thereof. Z may be selected from the group of an oxygen-containing unidentate or bidentate ligand, a sulfur-containing unidentate or bidentate ligand, a nitrogen-containing unidentate or bidentate ligand, a halogen-containing unidentate or bidentate ligand and a combination thereof, or an oxygen-containing unidentate or bidentate ligand; or an oxygen-containing unidentate or bidentate ligand containing at least one functional group. The functional group may be, for example, a carboxyl acid group, an amino-group, a hydroxy group, a thiol group, and a combination thereof. For all the above-mentioned ligands, at least one nitrogen, oxygen, halogen, sulfur, or phosphorous atom should be directly-connected to platinum center via unpaired electron pairs, which can form coordinate covalent bond with platinum center; thus, these groups can connect with platinum center and become the ligands of platinum complexes. In an embodiment herein, the ligand is a nitrogen-, oxygen-, and/or halogen-containing ligand, as it is believed that most current clinical platinum drugs contain these three kinds of ligands. It is believed that nitrogen, oxygen, halogen, sulfur, and phosphorous are excellent coordination atoms, they can easily form coordination bonds with platinum through unidentate, bidentate, or tridentate ligands. The unidentate, bidentate, and tridentate ligands of above ligands for developing platinum complexes are widely reported in many papers, some examples of which are indicated below:

Nitrogen- or halogen-containing unidentate ligands

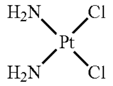

Cisplatin
(Clinical drug)

Nitrogen-, oxygen-, or halogen-containing unidentate and bidentate ligands

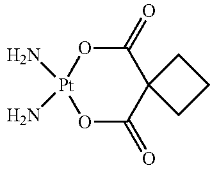

Carboplatin
(Clinical drug)

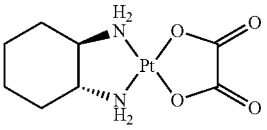

Oxaliplatin
(Clinical drug)

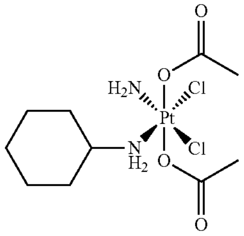

Satraplatin
(Phase III drug candidate)

Nitrogen-containing tridentate ligands

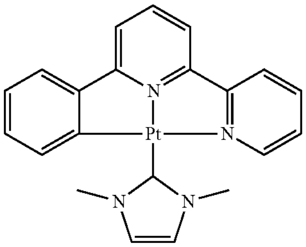

*Chem. Sci.*, 2011, 2, 728

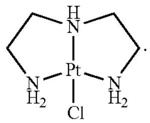

*Can. J. Chem.*, 1975, 53, 1139

-continued

Sulfur-containing unidentate and bidentate ligands

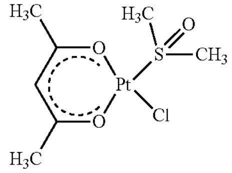

*BioMetals*, 2017, 30, 609

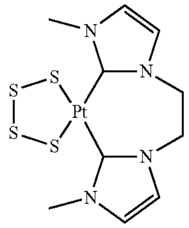

*Dalton Trans.*, 2012, 41, 12038

Phosphorus-containing unidentate and bidentate ligands

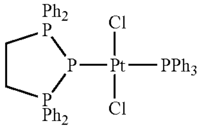

*Inorg. Chem.* 2012, 51, 9799

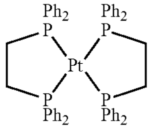

*Inorg. Chem.* 2012, 51, 9799

In Formula I, $R_1$~$R_5$ are each independently a functional group and together with the chromen-2-one moiety are referred to as the "aromatic portion". The functional group may be selected from the group consisting of a hydrogen atom, a hydrocarbon group that containing 1-50 carbon atoms, a nitrogen-containing group that containing 1-50 nitrogen or carbon atoms with the nitrogen directly-connect to the main ring structure, an oxygen-containing group that containing 1-50 oxygen or carbon atoms with the oxygen directly-connect to the main ring structure, a phosphorous-containing group that containing 1-50 phosphorous or carbon atoms with the phosphorous directly-connect to the main ring structure, a sulfur-containing group that containing 1-50 sulfur or carbon atoms with the sulfur directly-connect to the main ring structure, a halogen with the halogen directly-connect to the main ring structure and a combination thereof; or a hydrogen atom, a hydrocarbon group containing 1-50 carbon atoms, a nitrogen-containing group that containing 1-50 nitrogen or carbon atoms with the nitrogen directly-connect to the main ring structure, an oxygen-containing group that containing 1-50 oxygen or carbon atoms with the oxygen directly-connect to the main ring structure; and a combination thereof; or a hydrogen atom, a nitrogen-containing group that containing 1-50 nitrogen or carbon atoms with the nitrogen directly-connect to the main ring structure, and a combination thereof. In an embodiment herein, $R_1$-$R_5$ together with the main ring structure are derivatives of coumarin or rhodamine. It is believed that by changing $R_1$-$R_5$, the obtained coumarin or rhodamine derivatives can be tuned to present various photo properties (e.g. different excitation and emission wavelengths). Accordingly, the various treatment objectives, the photo properties and photooxidation properties of the platinum(IV) complexes may be tuned by choosing the appropriate derivatives. For example, for skin cancer treatment, platinum(IV) complexes with relatively shorter excitation wavelength may be preferred, since the shorter wavelength light possesses higher energy, which could activate the Pt(IV) complexes more effectively as deep penetration is not needed for areas closer to the skin surface; whereas for bladder cancer treatment, platinum(IV) complexes with longer excitation wavelength is preferred, because the tumor will typically be located deeper in the body; therefore a longer wavelength light with better tissue penetration may be required. Some examples of coumarin and rhodamine derivatives useful herein and their excitation wavelengths (Ex) are provided below:

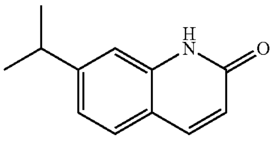

Ex = 352 nm

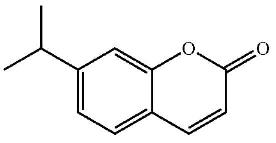

Ex = 371 nm

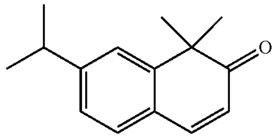

Ex = 413 nm

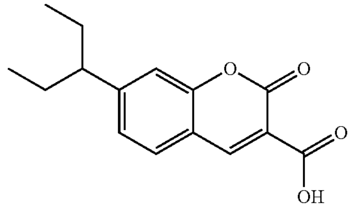

Ex = 430 nm

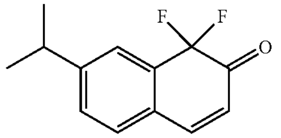

Ex = 491 nm

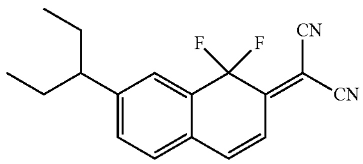

Ex = 600 nm

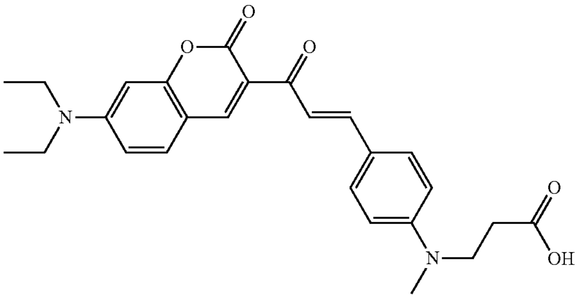

Ex = 470 nm (one photon excitation)
880 nm (two photon excitation)

-continued

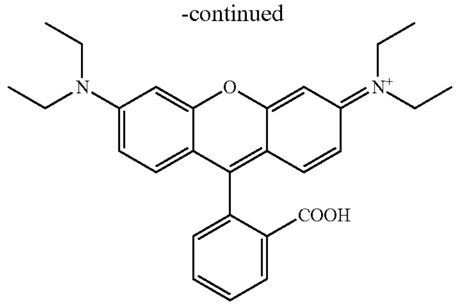

Ex = 546 nm

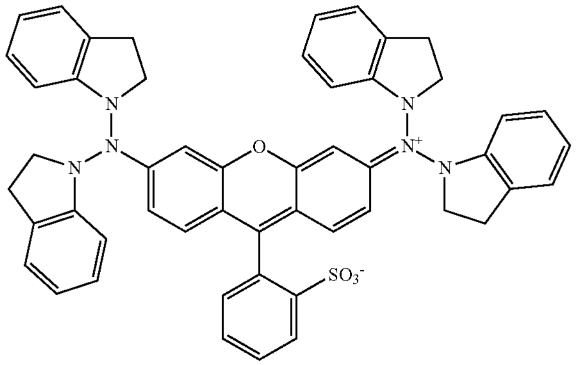

Ex = 660 nm

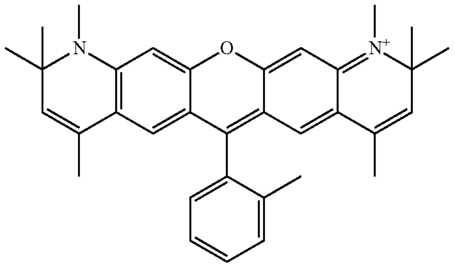

Ex = 712 nm

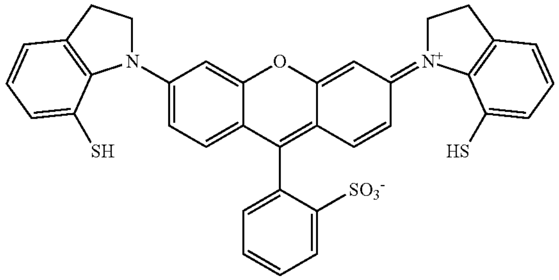

Ex = 779 nm

In Formula I, L is a linker unit which connects the platinum-containing portion and the aromatic portion. In an embodiment herein, the linker is selected from the group of a conjugated carbon ring containing structure with the total carbon number less than 26, a $C_{2-10}$ carbon chain, and a combination thereof, or at least one electron-donating moiety.

In Formula I, n indicates the charge of the complex, and may be zero (0), a positive charge, or a negative charge; or zero or a positive charge; or an integer from −2 to 4; or zero.

The present invention provides a novel class of platinum (IV) complexes. Without intending to be limited by theory, it is believed that these complexes are photo-oxidants that can be used as drugs and prodrugs; or prodrugs, and effectively activated by near-infrared radiation (NIR) for the treatment of diseases, especially cancer and bacterial infection. Compared with other UV or visible light photoactivatable drugs and prodrugs, the invented current platinum(IV) complexes may be activated by a low-dose of NIR to release platinum(II) drugs. It is believed that by using NIR instead of, for example, UV light, to activate the platinum(IV) complexes herein, the treatment and use possesses significantly increased penetration depth, and/or decreased phototoxicity. As the present platinum(IV) complexes are strong photo-oxidants, it is believed that they may oxidize biomolecules to further enhance their anticancer and antibacterial efficiency.

Furthermore, as compared to, for example, typical chemotherapy drugs, it is believed that the present complexes may be controllably activated in or near, for example, a tumor, a cancerous tissue, a cancerous region, an infection, etc. by NIR irradiation so as to reduce the side effects and damage to cells other parts of the subject. Upon photoactivation, the present complexes may effectively oxidize intracellular biomolecules such as proteins and lipids, and/or disrupt the intracellular redox hemostasis to eliminate cancer cells. By doing so, the invention herein effectively overcomes the resistance of cancer cells towards conventional chemotherapeutic agents. Since the present platinum(IV) complexes may directly oxidize intracellular biomolecules, bacteria and/or cancer cells in an oxygen-independent manner, they may provide improved biological activity while simultaneously-addressing the limitations of the hypoxic tumor microenvironment have to responding to conventional platinum drugs and photodynamic therapy (PDT) agents.

Embodiments of the present invention related to the preparation of the compounds and complexes herein, their cytotoxicity against various tumors and/or cancer cell lines, and their antibacterial activities. An embodiment of the invention also relates to a pharmaceutical composition comprising at least one photo-activatable platinum(IV) photo-oxidant and a pharmaceutically-acceptable carrier. It is also believed that an embodiment of the platinum(IV) complex herein may be useful as, for example, an anticancer agent, a photodynamic therapeutic agent, a photo-oxidant and a combination thereof; or an anticancer agent; a photodynamic therapeutic agent; or a photo-oxidant.

Without intending to be limited by theory, it is believed that the compounds of the present invention are photoactivatable by NIR such as that having a wavelength of from about 700 nanometers (nm) to about 1400 nm; or from about 800 nm to about 1100 nm; or from about 800 nm to 1000 nm. It is believed that when activated by NIR in this range, the platinum(IV) complexes herein; or the photoactivatable platinum(IV) prodrugs herein, may provide significant cytotoxicity against various cancer cells, including platinum drug-resistant cancer cells.

It is further believed that, as compared with current platinum drugs, the platinum(IV) complexes herein possess a variety of advantages such as, for example, controllable activation, significant penetration ability, significantly reduced cytotoxicity, and the potential to reduce or even prevent bacteria from developing drug resistance. In addition, as compared with conventional photosensitizers, it is believed that the platinum(IV) complexes herein possess a much longer activation wavelength. It is believed that this advantageously enables them to be used at a greater depth from the photoactivation device, and therefore at a greater tissue depth. This in turn allows improved efficacy and greater penetration capacity. Furthermore, as the present platinum(IV) complexes do not require oxygen for activation/efficacy, the present complexes may possess biological activity irrespective of whether oxygen is present, even under hypoxia, and thus are more flexible and versatile than existing oxygen-dependent photosensitizers, drugs, and prodrugs.

It is also believed that as the present platinum(IV) complexes may become strong oxidants upon photoexcitation so they may also robustly destroy components such as, for example, lipopolysaccharides or proteins such as those in a bacterial cell wall (if present) and/or a bacterial cell membrane so as to lyse and kill the bacteria. It is further believed that the present platinum(IV) complexes may also attack intracellular survival-related biomolecules, such as DNA, glutathione (GSH), and hemin, etc. Without intending to be limited by theory it is believed that as the present platinum (IV) complexes aim to damage bacterial cell walls and membranes, they will not create or lead to cross-resistance with conventional antibiotics. Therefore, it is believed that the present invention may overcome certain barriers for conventional APDT agents. It is believed that the complexes herein may damage multiple, many or even all biological components of the cell membrane, we can specifically activate complexes in the tumor region by irradiation this region with NIR light. Also, these complexes can be further conjugated with tumor-targeting groups, such as antibody or tumor-targeting peptides, to enhance the tumor-targeting ability.) Thus it is understood that the present platinum(IV) complexes may be generally classified as a drug; or as a prodrug.

In an embodiment herein, the power of the NIR may be from about 0.01 W/cm$^2$ to about 4 W/cm$^2$; or from about 0.1 W/cm$^2$ to about 2 W/cm$^2$; or from about 0.2 W/cm$^2$ to about 0.8 W/cm$^2$, as this range is considered strong enough to both penetrate and activate the complexes herein, while also being safe for use on tissues, such as human tissues to reach the platinum(IV) complexes lying under the skin. In an embodiment herein, the power source is selected from the group of a continue-wavelength laser, a pulsed laser, and a combination thereof. In an embodiment herein, the pulsed laser has an emission frequency higher than 1 MHz. Without intending to be limited by theory, it is believed that as such NIR may be applied externally, and as NIR may be less damaging than, for example, UV light, which, due to its short wavelength and high energy, may potentially cause, for example, cancer, genetic damage, etc. Thus, unlike other photoactivatable prodrugs, which are activated by UV or visible light, it is believed that the present platinum(IV) complexes are suitable for use as drugs and/or prodrugs that can be activated by low-dosed near-infrared radiation (e.g., 880 nm, 0.4 W/cm$^2$). Without intending to be limited by theory, it is believed that the use of NIR in the present invention may significantly improve the penetration depth during treatment and/or decrease phototoxicity from irradiation.

In an embodiment herein, the platinum(IV) complex is selected from the group of

Formula II(a)

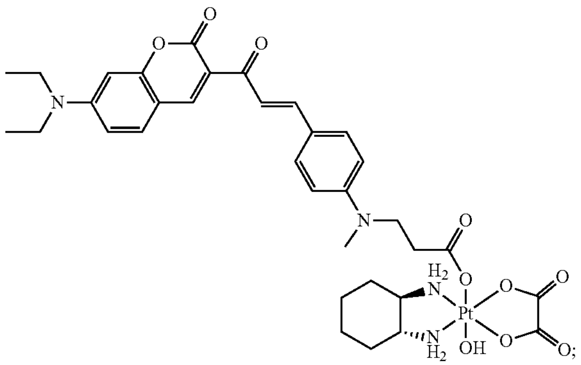

;

Formula II(b)

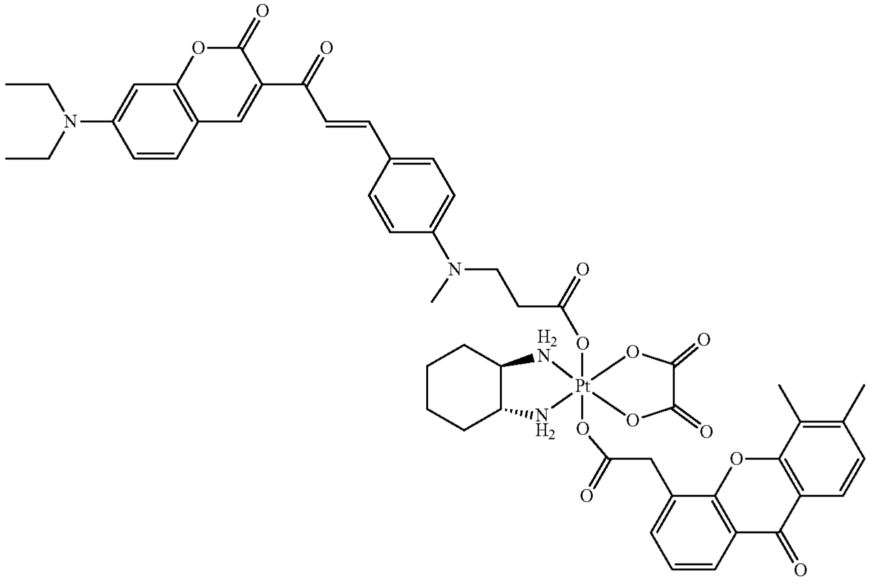

-continued

Formula II(c)

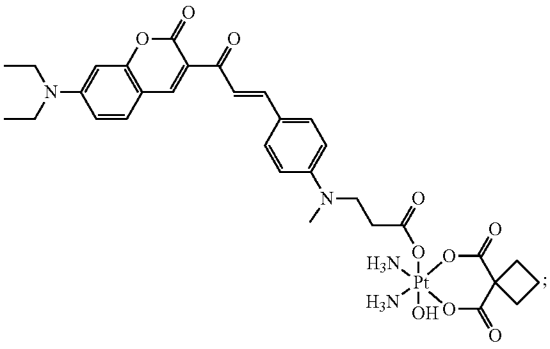

; and

Formula II(d)

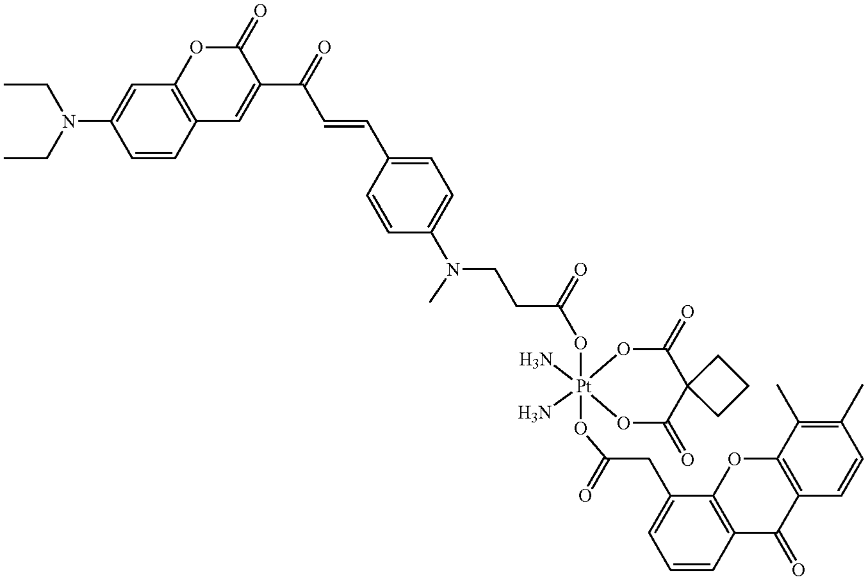

An embodiment of the present invention relates to a pharmaceutical composition containing a platinum(IV) complex; or a platinum(IV) complex as described herein. The pharmaceutical composition may further contain an ingredient selected from the group of, for example, an additional anti-cancer agent, an adjuvant, an antibody, a binder, a buffer, a diluent, a filler, a pharmaceutically-acceptable carrier, a preservative, a surfactant, a contrast media, a radioactive agent, a photodynamic therapy agent, a photothermal therapy agent, an ultrasonic therapy agent, and a combination thereof; or an additional anti-cancer agent, an antibody, an adjuvant, a buffer, a pharmaceutically-acceptable carrier, and a combination thereof, or an antibody, a pharmaceutically-acceptable carrier and a combination thereof, as well as other pharmaceutical components known in the art.

In an embodiment herein, the antibody, peptide, and specifical tumor/bacteria targeting groups useful herein may, for example, linked to the platinum(IV) complex herein and may also be targeted against the cancer, tumor, or infection/bacteria. Thus, it is believed that the platinum(IV) complex herein will be drawn to and/or concentrated at the location of the cancer, tumor and/or infection, so as to enhance its effectiveness during use.

An embodiment of the present invention relates to a method of manufacturing the platinum(IV) complex of Formula II(a) according to the steps of providing c,c,t-[Pt(DACH)$(OH)_2$(ox)], providing a N-hydroxysuccinimide (NHS) ester of 3-((4-(3-(7-(diethylamino)-2-oxochroman-3-yl)-3-oxoprop-1-en-1-yl)phenyl)(methyl)amino)propanoic acid, and reacting c,c,t-[Pt(DACH)$(OH)_2$(ox)] with the NHS ester of 3-((4-(3-(7-(diethylamino)-2-oxochroman-3-yl)-3-oxoprop-1-en-1-yl)phenyl)(methyl)amino)propanoic acid to form the platinum(IV) complex of Formula II(a). Without intending to be limited by theory, it is believed that this manufacturing method is efficient, easy, and scalable.

c,c,t-[Pt(DACH)$(OH)_2$(ox)]:

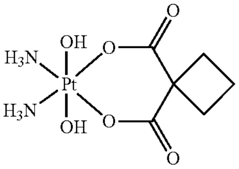

.

NHS ester of 3-((4-(3-(7-(diethylamino)-2-oxochroman-3-yl)-3-oxoprop-1-en-1-yl)phenyl)(methyl)amino)propanoic acid:

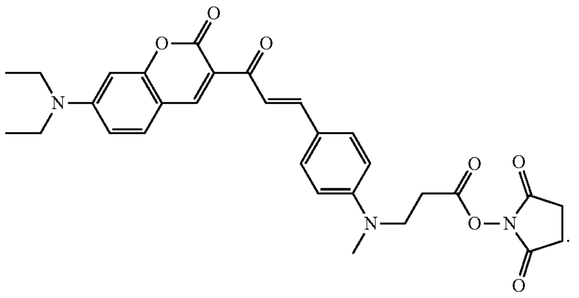 [SMILES: CCN(CC)c1ccc2cc(C(=O)/C=C/c3ccc(N(C)CCC(=O)ON4C(=O)CCC4=O)cc3)c(=O)oc2c1]

Once synthesized, these complexes are spectroscopically characterized, and their activities against various cancer cell lines and different bacterial species are analyzed. The mechanism of action of some platinum(IV) complexes is further analyzed.

Without intending to be limited by theory, it is believed that platinum(IV) complexes are their highest oxidation state (at or higher than 1.23 V) and since they cannot be further oxidized, they are more likely to be reduced after photoexcitation. Furthermore, while other metal complexes (e.g., Ru, Ir, and Rh) which may also exhibit photooxidation ability at their highest oxidation state, it has been found that platinum(IV) complexes containing two axial ligands are easily functionalized. Consequently, during the photoreduction of the platinum(IV) complexes herein, the two axial ligands will typically be released, making the platinum(IV) complexes more flexible to design with multifunctional prodrugs. Accordingly, in an embodiment herein, the releasable ligand may itself possess anti-cancer and/or drug activity.

In addition, several platinum complexes have been approved as anticancer drugs for clinical treatments, thus potentially-reducing regulatory hurdles. In particular, it is believed that the present designed NIR light-activatable platinum(IV) complexes may also serve as prodrugs to controllably release the clinical drugs for precise and directed treatment. Therefore, it is believed that platinum (IV) complexes are especially suited as NIR activatable prodrugs for the treatment and/or elimination of cancer cells and/or infection such as that caused by bacteria through the release of clinical drugs and/or photooxidation.

Therefore it is understood that upon activation with NIR, photoexcitation causes the present platinum(IV) complexes to transform into strong oxidants, which can subsequently oxidize intracellular biomolecules, such as proteins and lipids, generate ROS, lipid peroxides, and protons. Upon exposure to NIR, it is believed that these platinum(IV) complexes may easily oxidize surrounding molecules and may be reduced to platinum(II), releasing the two axial ligands. Most intracellular biomolecules, such as protein and lipids are easily oxidized; therefore, during this photoreduction progress it is believed that the existing intracellular biomolecules can serve as the electron donors and be oxidized, leading to the creation of reactive oxygen species (ROS), lipid peroxides, and protons which may further inhibit and/or attack cancer, the infection, bacteria, etc.

The ROS and oxidized lipid may disrupt the cell's intracellular redox balance, trigger intense oxidative stress to initiate cell death, and/or cause the protons to break intracellular pH homeostasis so as to synergistically kill cancer cells and overcome traditional drug resistance. At the same time, it is believed that these complexes will be reduced and release the photo-sensitive ligands and platinum(II) drug. It is believed that the platinum(II) drug may serve as PDT agents to further enhance the therapeutic effect.

In an embodiment herein the method of manufacturing a platinum(IV) complex of Formula II(b) contains the steps of providing a platinum(IV) complex of Formula II(a), providing an NHS ester of 5,6-dimethylxanthenone-4-acetic acid (i.e., ligand 3), and reacting the platinum(IV) complex of Formula II(a) with the NHS ester of 5,6-dimethylxanthenone-4-acetic acid to form the platinum(IV) complex of Formula II(b). Without intending to be limited by theory, it is believed that this manufacturing method is efficient, easy, and scalable.

In an embodiment herein a method for manufacturing a platinum(IV) complex of Formula II(c) contains the steps of providing diammine (cyclobutane-1,1 dicarboxylato) dihydroxido platinum(IV), providing a NHS ester of 3-((4-(3-(7-(diethylamino)-2-oxochroman-3-yl)-3-oxoprop-1-en-1-yl)phenyl)(methyl)amino)propanoic acid, and reacting diammine (cyclobutane-1,1 dicarboxylato) dihydroxido platinum(IV) with the NHS ester of 3-((4-(3-(7-(diethylamino)-2-oxochroman-3-yl)-3-oxoprop-1-en-1-yl)phenyl)(methyl)amino)propanoic acid to form the platinum(IV) complex of Formula II(c). Without intending to be limited by theory, it is believed that this manufacturing method is efficient, easy, and scalable.

In an embodiment herein, a method for manufacturing a platinum(IV) complex of Formula II(d) contains the steps of providing the platinum(IV) complex of Formula II(c), providing a NHS ester of 5,6-dimethylxanthenone-4-acetic acid:

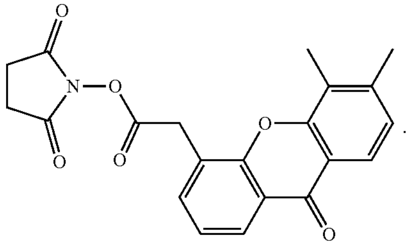 [SMILES: Cc1ccc2c(=O)c3cccc(CC(=O)ON4C(=O)CCC4=O)c3oc2c1C]

The platinum(IV) complex of Formula II(c) reacts with the NHS ester of 5,6-dimethylxanthenone-4-acetic acid to form the platinum(IV) complex of Formula II(d). Without intending to be limited by theory, it is believed that this manufacturing method is efficient, easy, and scalable.

In an embodiment herein, the complex according to Formula I may include, for example, derivatives of salicylaldehyde, acetoacetic acid, ethyl acetate, derivatives of 3-oxobutanoate (e.g. methyl 3-oxobutanoate and phenyl 3-oxobutanoate), platinum(II) drugs and complexes (e.g. cisplatin, nedaplatin, and heptaplatin), anhydride derivatives (e.g. succinic anhydride), halogen, and carboxyl acid derivatives. We note that the ligands herein may be directly-attached to the platinum(IV) atom (i.e., equatorial ligands), or may be attached to the atoms or moieties attached to the platinum atom (i.e., axial ligands).

Without intending to be limited by theory it is also believed that an embodiment of the present invention may provide a method for treating cancer, a tumor, or an infection in a subject. In an embodiment herein such a method includes the steps of administering to the subject an effective dose of the platinum(IV) complex according to Formula I, and administering to the subject near-infrared radiation (NIR), typically the NIR is administered to the subject from the outside of the body while the platinum(IV) is located and/or where the cancer, tumor, or infection is treated in vivo.

Thus, the cancer, tumor, or infection is typically in a sub-dermal location in the subject. In an embodiment herein, the sub-dermal location is from about 0.01 cm to about 2 cm; or from about 0.05 cm to about 1 cm away from the irradiation site; or under the irradiation site. In an embodiment herein, where the cancer, tumor, or infection is deep within the subject (i.e., more than about 2 cm below the surface of the skin, then an optical fiber; or a laparoscopic optical fiber, may be employed to deliver the NIR to the sub-dermal location.

As the effective dose of a medication is often dependent upon the weight of the patient/subject, in an embodiment herein, the effective dose is from about 0.1 mg/kg to about 90 mg/kg; or from about 0.5 mg/kg to about 60 mg/kg; or from about 1.5 mg/kg to about 30 mg/kg, based on the weight of the patient.

It has also been found that the present invention may be especially effective in subjects where the cancer or the tumor exhibits cisplatin resistance, platinum resistance, photodynamic therapy (PDT) resistance, etc. and thus, in an embodiment herein, the composition, treatment and/or method herein is directed towards a subject having a cancer or tumor exhibiting cisplatin resistance, platinum resistance, PDT resistance, and a combination thereof. In an embodiment herein, the cancer or tumor is of a cancer selected from the group of breast cancer, peritoneal cancer, ovarian cancer, lung cancer, and a combination thereof; or ovarian cancer, as these have been shown to sometimes exhibit platinum resistance It has also been found that the platinum(IV) complexes herein may also be useful in treating a bacterial infection; or a bacterial infection caused by bacteria selected from Gram-negative bacteria, Gram-positive bacteria, and a combination thereof; or Gram-positive bacteria.

In an embodiment herein, the invention herein may be used in conjunction with, for example, radiotherapy, ultrasonic therapy, immune therapy, gene therapy, etc. and combinations thereof so as to enhance the effectiveness of the treatments.

Alternatively, an embodiment of the invention relates to the use of a platinum(IV) complex according to Formula I in the manufacture of a medicament for the treatment of cancer, a tumor, an infection, and a combination thereof, in a subject. An embodiment of the invention herein relates to the use of a platinum(IV) complex according to Formula I for the treatment of cancer, a tumor, an infection, and a combination thereof, in a subject.

Example 1

Synthesis: embodiments of the platinum(IV) complex of the present invention are synthesized herein as the following compounds.

FIG. 1 shows an embodiment of synthesis steps for complex 4 and complex 5.

Synthesis of compound 1 in FIG. 1: Ethyl acetoacetate (1.9 mL), piperidine (125 μL), and 4-diethylaminosalicylaldehyde (0.48 g) are added into 20 mL ethanol to stir and reflux for 12 h. Then a NaOH solution (3 M, 20 mL) is added to reflux for another 3 h. After the reaction, the mixture is cooled down to room temperature, and HCl solution (37%) is added to adjust the pH value to 2.0 to precipitate the product. After centrifugation, the crude product is collected and recrystallized in ethanol to get the pure product (yield: 80%, purity: 99%).

Figure 3:
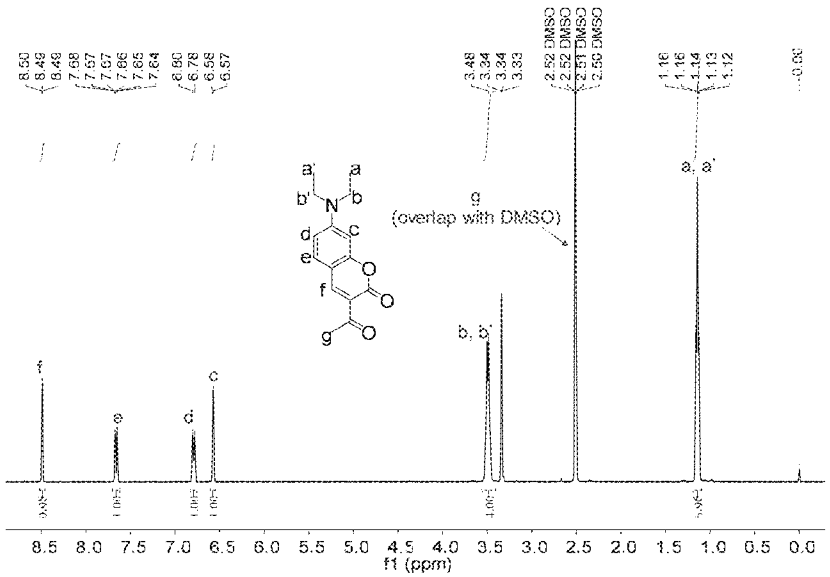
FIG. 3 shows a $^1$H NMR analysis of compound 1 in DMSO-d6.

FIG. 3 shows a $^1$H NMR analysis of compound 1 in DMSO-d6. $^1$H NMR (400 MHz, DMSO-d6) δ 8.49 (m, 1H), 7.66 (dt, J=8.9, 2.3 Hz, 1H), 6.79 (d, J=9.2 Hz, 1H), 6.58 (d, J=3.4 Hz, 1H), 3.48 (d, 4H), 2.37 (s, 3H), 1.19-1.09 (m, 6H). ESI-MS: m/z=260.3 $[M+H]^+$.

Synthesis of compound 2 in FIG. 1: Commercially available N-methyl-N-cyanoethyl-4-aminobenzaldehyde (1.0 g) is added into 30 mL NaOH solution (5 M). Then 3 mL 30% $H_2O_2$ is added to reflux for 4 h. Cool the solution to room temperature, using HCl to adjust the pH to 2.0. Extract the crude compound by 100 mL ethyl acetate, and purify the compound by silica column, eluent by petroleum ether/ethyl acetate. Remove the solvent, compound 2 is collected as a pink power (yield: 65%, purity: 97%).

Figure 4:
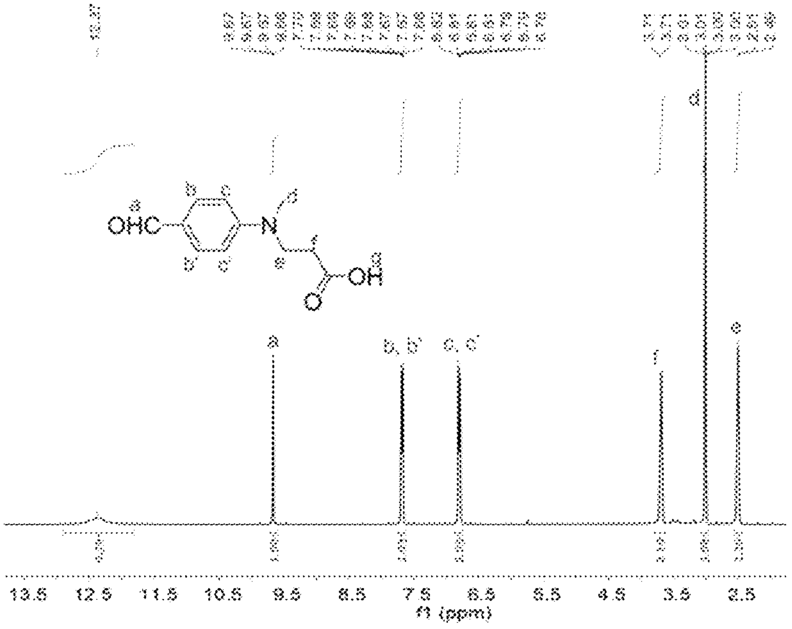
FIG. 4 shows a $^1$H NMR analysis of compound 2 in DMSO-d6.

FIG. 4 shows a $^1$H NMR analysis of compound 2 in DMSO-d6. $^1$H NMR (400 MHz, DMSO-d6) δ 12.37 (s, 1H), 9.71-9.60 (m, 1H), 7.68 (dd, J=9.0, 3.1, 1.6 Hz, 2H), 6.88-6.74 (m, 2H), 3.71 (d, J=3.1 Hz, 2H), 3.07-2.97 (m, 3H), 2.50 (d, J=7.6 Hz, 2H). ESI-MS: m/z=206.3 $[M-H]^-$.

Synthesis of ligand 3 in FIG. 1: (i.e., NHS ester of 3-((4-(3-(7-(diethylamino)-2-oxochroman-3-yl)-3-oxoprop-1-en-1-yl)phenyl)(methyl)amino)propanoic acid): Compound 1 (200 mg) and compound 2 (250 mg) are added into 25 mL dichloromethane, 0.1 mL triethylamine is then added. The mixed solution is refluxed for 72 h. Then the solvent is removed, and the crude product purified by silica column. Petroleum ether (50%)+ethyl acetate (50%) is used as eluent solution to give the pure ligand 3 (yield: 42%, purity: 97%).

Figure 5:
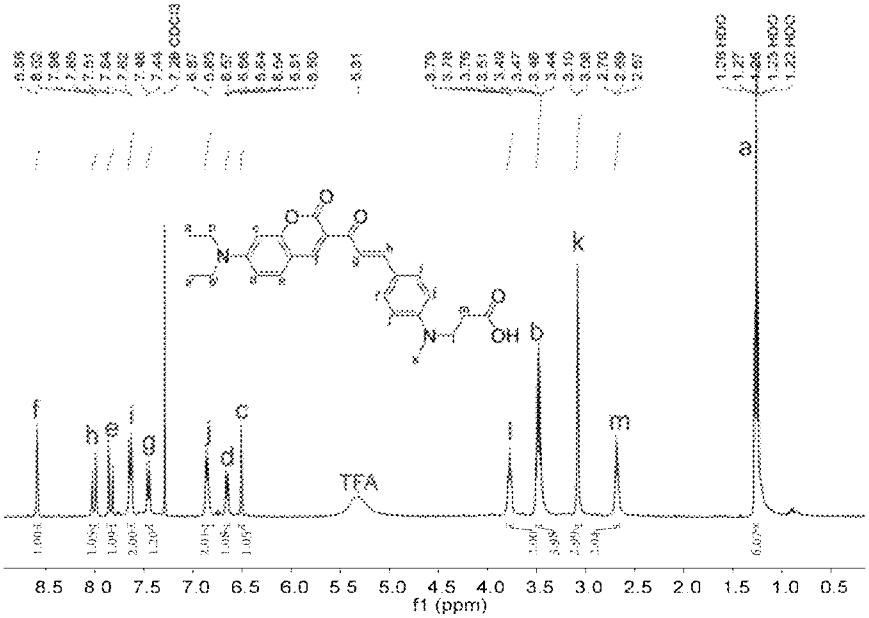
FIG. 5 shows a $^1$H NMR analysis of ligand 3 in $CDCl_3$.

FIG. 5 shows a $^1$H NMR analysis of ligand 3 in $CDCl_3$. $^1$H NMR (400 MHz, Chloroform-d) δ 8.58 (s, 1H), 8.00 (d, J=15.5 Hz, 1H), 7.83 (d, J=15.5 Hz, 1H), 7.63 (d, J=8.3 Hz, 2H), 7.45 (d, J=8.9 Hz, 1H), 6.86 (d, J=8.3 Hz, 2H), 6.65 (dd, J=9.0, 2.4 Hz, 1H), 6.51 (d, J=2.3 Hz, 1H), 3.78 (t, J=7.2 Hz, 2H), 3.47 (t, J=7.1 Hz, 4H), 3.08 (s, 3H), 2.69 (t, J=7.0 Hz, 2H), 1.26 (d, J=7.2 Hz, 6H).).

Figure 6:
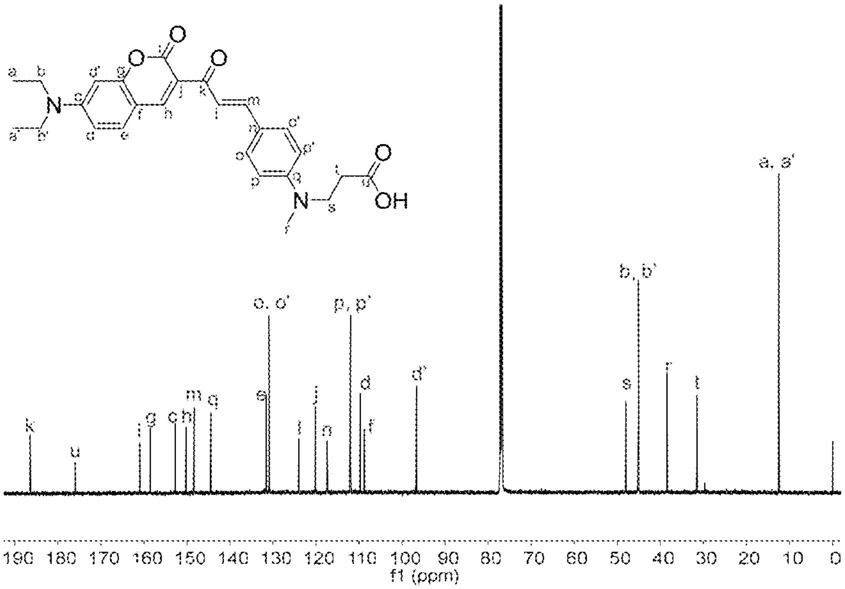
FIG. 6 shows a $^{13}$C NMR analysis of ligand 3 in $CDCl_3$.

FIG. 6 shows a $^{13}$C NMR analysis of ligand 3 in $CDCl_3$. $^{13}$C NMR (151 MHz, CDCl3) δ(ppm): 12.50, 31.54, 38.48, 45.13, 48.07, 96.66, 108.74, 109.72, 112.01, 117.44, 120.20, 123.99, 130.91, 131.61, 144.47, 148.32, 150.18, 152.73, 158.50, 160.96, 175.96, 186.40.

Figure 7A:
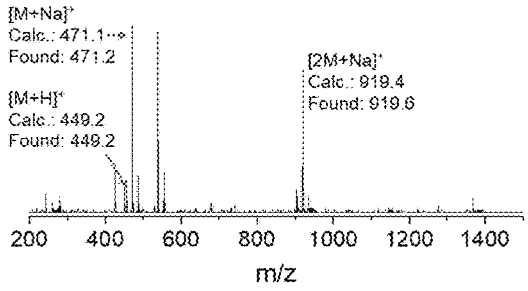
FIG. 7A shows an ESI-MS analysis of ligand 3.
Figure 7B:
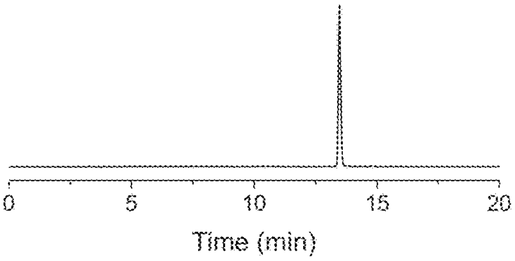
FIG. 7B shows an HPLC chromatograph of ligand 3.

FIG. 7A shows an ESI-MS (electrospray ionization mass spectroscopy) analysis of ligand 3: m/z=471.2 $[M+Na]^+$, m/z=449.2 $[M+H]^+$. FIG. 7B shows a HPLC chromatograph of ligand 3.

Synthesis of complex 4 (i.e., Formula II(c)) in FIG. 1: Ligand 3 (44.8 mg, 0.1 mmol) and diammine (cyclobutane-1,1 dicarboxylato) dihydroxido platinum(IV) (36 mg, 0.09 mmol) are mixed in 4 mL DMSO, 2-(1H-benzotriazole-1-yl)-1,1,3,3-tetramethylaminium tetrafluoroborate (TBTU, 48.2 mg, 0.15 mmol) and triethylamine (15 mg, 0.15 mmol) are added into the solution to stir at 50° C. for 12 h. After reaction, 5 mL DCM, 5 mL acetone and 35 mL diethyl ether are added to precipitate the crude product. After centrifugation, the crude product is collected and purified by HPLC to give complex 4. Yield: 64%, purity: 95%.

Figure 8:
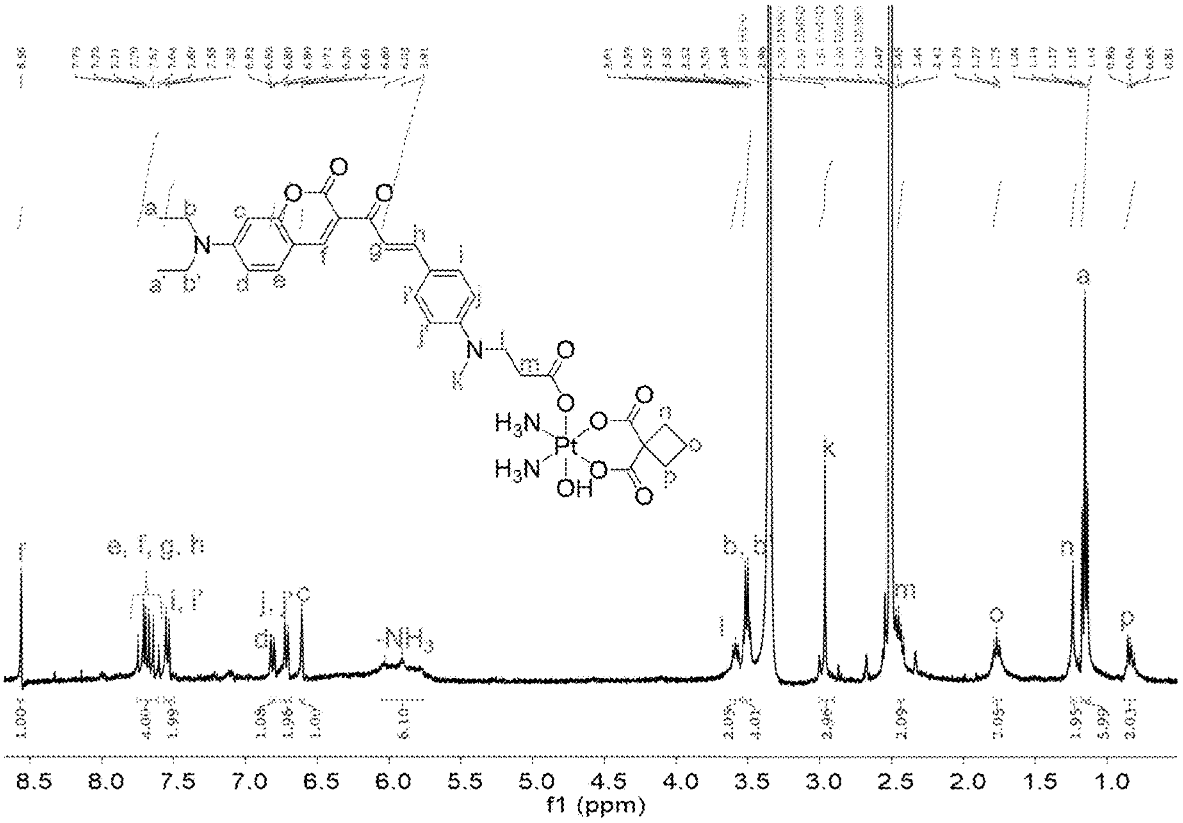
FIG. 8 shows a $^1$H NMR analysis of complex 4 in DMSO-d6.

FIG. 8 shows a $^1$H NMR analysis of complex 4 in DMSO-d6. $^1$H NMR [dimethyl sulphoxide-d6 (DMSO-d6), 400 MHz δ/ppm 8.56 (s, 1H), 7.71-7.53 (m, 5H), 6.81 (d, J=8.9 Hz, 1H), 6.74 (d, J=8.7 Hz, 2H), 6.61 (d, J=2.3 Hz, 1H), 6.15-5.73 (m, 6H), 3.58 (d, 2H), 3.51 (q, J=6.9 Hz, 4H), 2.94 (s, 3H), 2.47 (s, 2H), 2.96 (d, 2H), 2.81 (d, 2H), 1.75 (m, 2H), 1.15 (q, J=15.5, 11.1 Hz, 6H), 0.84 (dd, J=10.5, 7.0 Hz, 2H).

Figure 9:
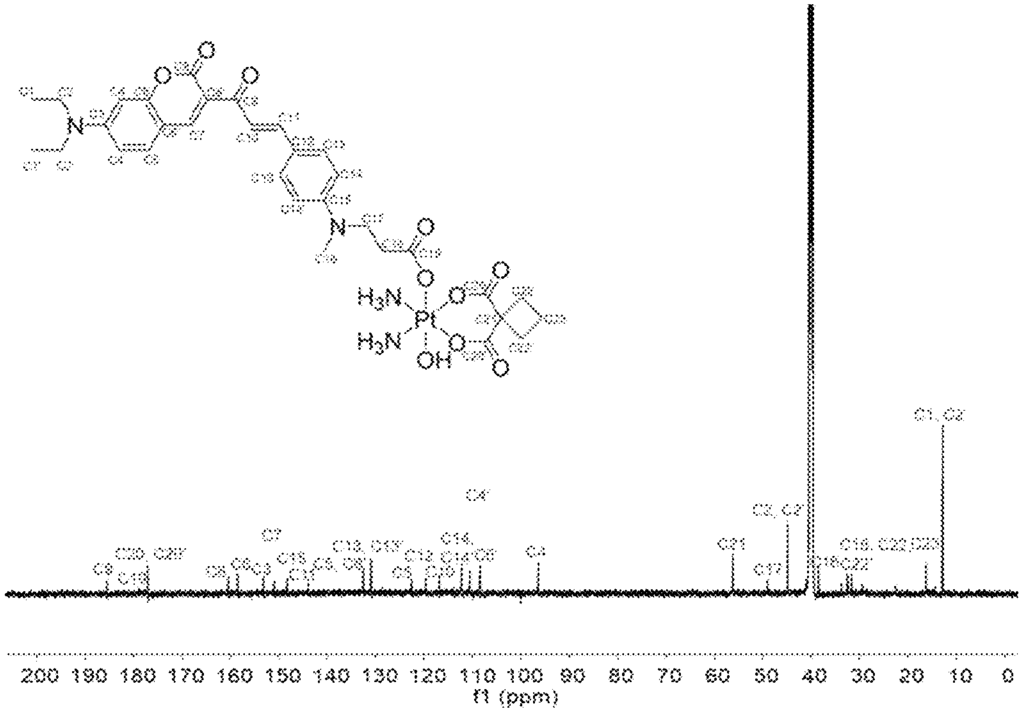
FIG. 9 shows a $^{13}$C NMR analysis of complex 4 in DMSO-d6.

FIG. 9 shows a $^{13}C$ NMR analysis of complex 4 in DMSO-d6. $^{13}C$ NMR (151 MHz, DMSO) δ(ppm): 12.85, 16.30, 29.46, 31.63, 32.54, 33.76, 38.50, 44.88, 49.02, 56.21, 96.37, 108.37, 110.53, 112.18, 116.80, 119.65, 122.52, 130.92, 132.53, 143.88, 148.22, 150.92, 153.17, 158.46, 160.41, 177.04, 178.87, 185.48.

Figure 10:
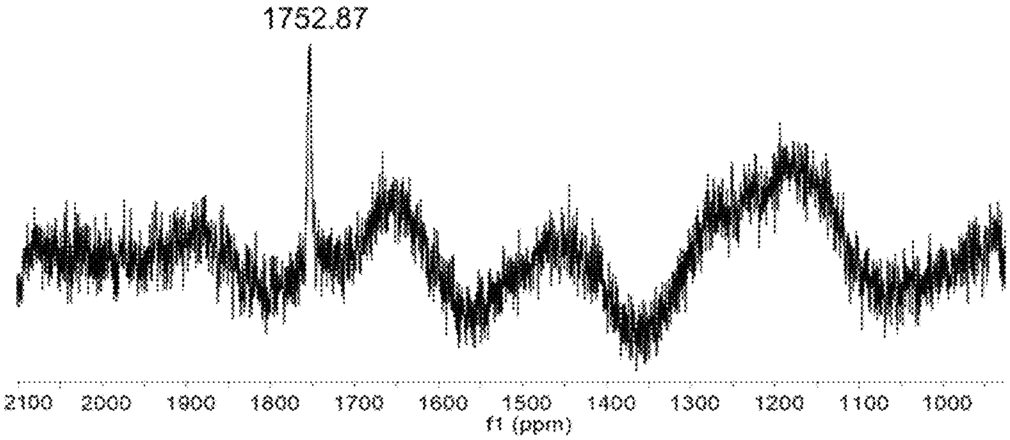
FIG. 10 shows a $^{195}$Pt NMR analysis of complex 4 in DMSO-d6.

FIG. 10 shows a $^{195}Pt$ NMR analysis of complex 4 in DMSO-d6. $^{195}Pt$ NMR (129 MHz, DMSO) δ(ppm): 1752.87.

Figure 11A:
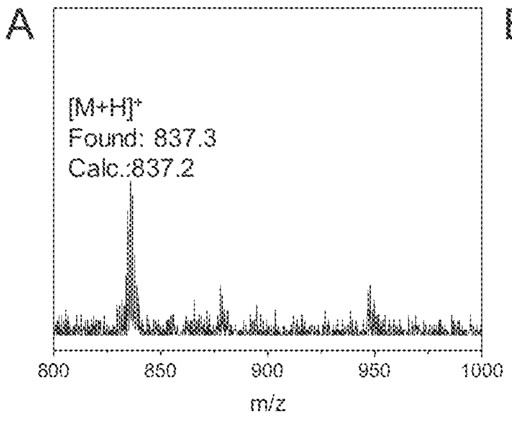
FIG. 11A shows an ESI-MS analysis of complex 4.
Figure 11B:
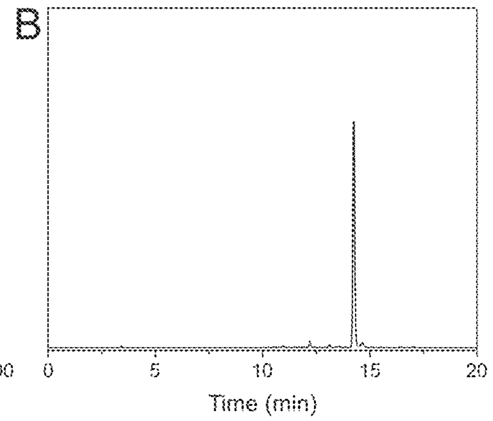
FIG. 11B shows an HPLC chromatograph of complex 4.

FIG. 11A shows an ESI-MS analysis of complex 4 (m/z): $[M+H]^+$ calculated for $C_{32}H_{41}N_{34}O_{10}Pt$: 837.3, found: 837.2. FIG. 11B shows an HPLC chromatograph of complex 4.

Synthesis of complex 5 (i.e., Formula II(a)) in FIG. 1: Ligand 3 (50 mg), $[Pt(DACH)(OH)_2(ox)]$ (40 mg), 2-(1H-Benzotriazole-1-yl)-1,1,3,3-tetramethylaminium tetrafluoroborate (TBTU, 40 mg) and 20 μL triethylamine are added into 3 mL DMF to stir at 50° C. for 12 h. After reaction, 5 mL acetone and 35 mL $EtO_2$ are added to precipitate the crude product. After centrifugation, the collected solid is purified by silica column, with ethyl acetate/methanol as the eluent solution. The solvent is removed by rotary evaporation and complex 5 is collected as a red powder and purified by HPLC (yield: 39%, purity: 96%).

Figure 12:
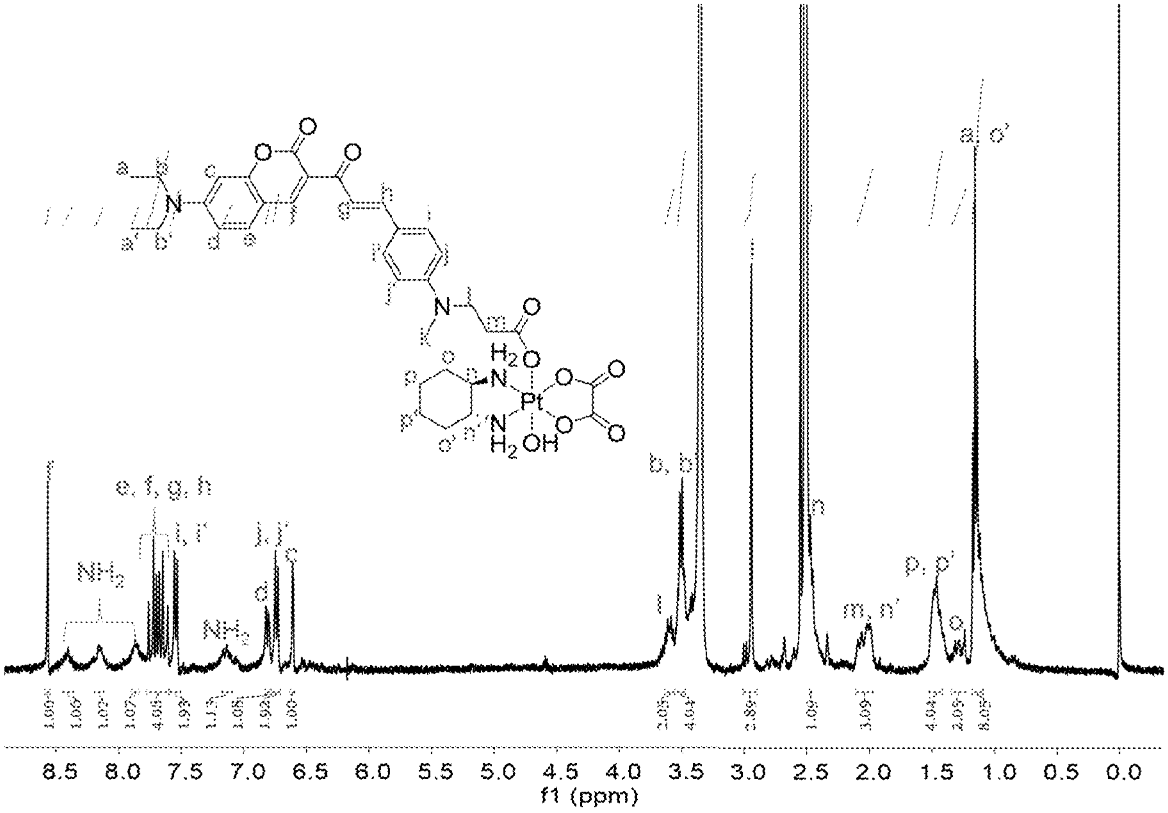
FIG. 12 shows a $^1$H NMR analysis of complex 5 in DMSO-d6.

FIG. 12 shows a $^1H$ NMR analysis of complex 5 in DMSO-d6. $^1H$ NMR [dimethyl sulphoxide-d6 (DMSO-d6), 400 MHz δ/ppm 8.57 (s, 1H), 8.41 (s, 1H), 8.15 (s, 1H), 7.86 (s, 1H), 7.78-7.60 (m, 4H), 7.54 (d, J=8.5 Hz, 2H), 7.14 (s, 1H), 6.81 (d, J=8.9 Hz, 1H), 6.74 (d, J=8.7 Hz, 2H), 6.61 (d, J=2.3 Hz, 1H), 3.62 (d, 2H), 3.51 (q, J=6.9 Hz, 4H), 2.94 (s, 3H), 2.47 (s, 2H), 2.04 (d, J=21.1 Hz, 2H), 1.47 (s, 4H), 1.35-1.23 (m, 2H), 1.14 (q, J=15.3, 11.1 Hz, 6H).

Figure 13:
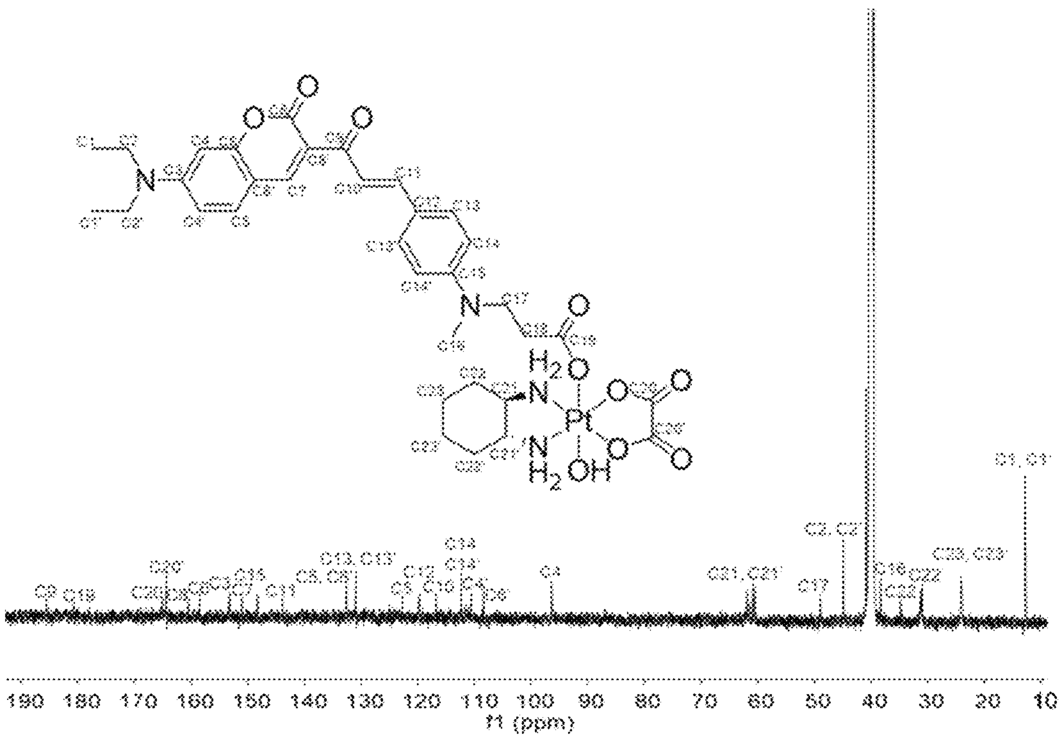
FIG. 13 shows a $^{13}$C NMR analysis of complex 5 in DMSO-d6.

FIG. 13 shows a $^{13}C$ NMR analysis of complex 5 in DMSO-d6. $^{13}C$ NMR (151 MHz, DMSO) δ(ppm): 12.84, 24.11, 24.21, 30.99, 31.20, 34.82, 38.33, 44.89, 48.95, 60.56, 60.87, 61.88, 96.35, 108.37, 112.33, 116.74, 119.71, 130.90, 132.55, 148.26, 150.98, 153.17, 158.48, 164.33, 180.67, 185.47.

Figure 14:
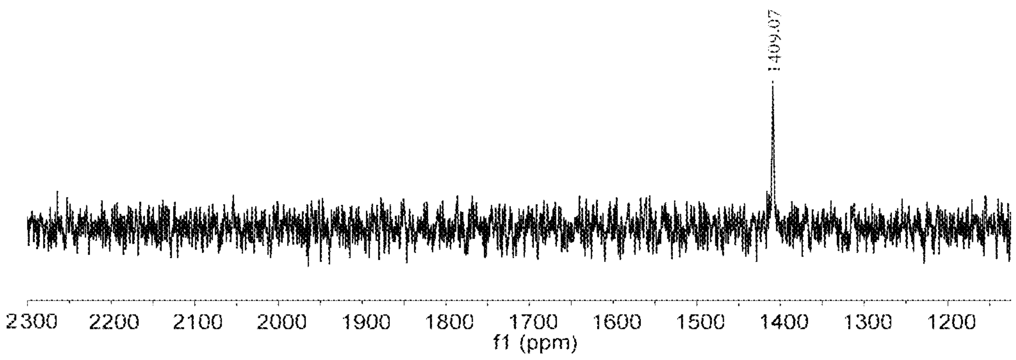
FIG. 14 shows a $^{195}$Pt NMR analysis of complex 5 in DMSO-d6.

FIG. 14 shows a $^{195}Pt$ NMR analysis of complex 5 in DMSO-d6. $^{195}Pt$ NMR (129 MHz, DMSO) δ(ppm): 1409.07.

Figure 15A:
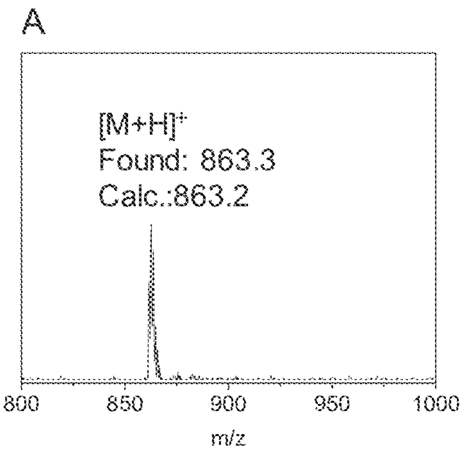
FIG. 15A shows an ESI-MS analysis for complex 5.
Figure 15B:
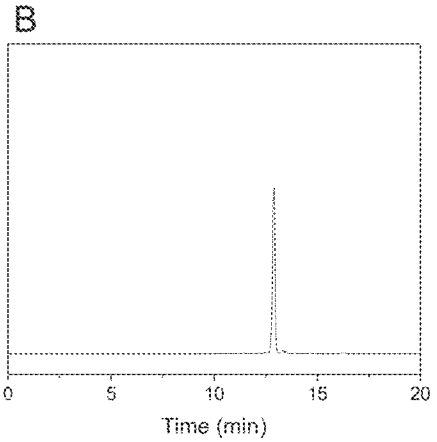
FIG. 15B shows an HPLC chromatograph of complex 5.

FIG. 15A shows an ESI-MS analysis for complex 5 (m/z): $[M+H]^+$ calculated for $C_{34}H_{43}N_4O_{10}Pt$: 863.3, found: 863.2. FIG. 15B shows a HPLC chromatograph of complex 5.

Example 2

Figure 2:
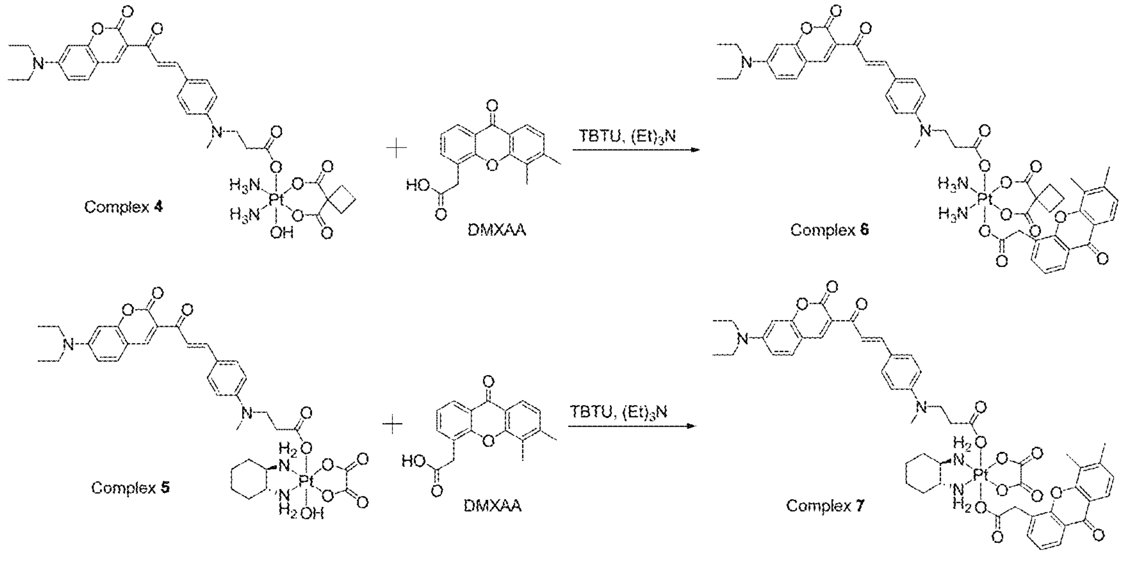
FIG. 2 shows an embodiment of the synthesis of complex 6 (i.e., Formula II(d)) and complex 7 (i.e., Formula II(b))

FIG. 2 shows an embodiment of the synthesis of complex 6 (i.e., Formula II(d)) and complex 7 (i.e., Formula II(b)).

Synthesis of complex 6 (i.e., Formula II(d)) in FIG. 2: Complex 4 (i.e., Formula II(c); 834 mg, 1 mmol) and vadimezan (DMXAA, 304 mg, 1.1 mmol) are mixed in 5 mL DMSO, TBTU (48.2 mg, 0.15 mmol) and triethylamine (15 mg, 0.15 mmol) are added into the solution to stir at 50° C. for 12 h. After reaction, 5 mL DCM, 5 mL acetone and 35 mL diethyl ether are added to precipitate the crude product. After centrifugation, the crude product is collected and purified by HPLC to give complex 6. Yield: 70%, purity: 96%.

Figure 16:
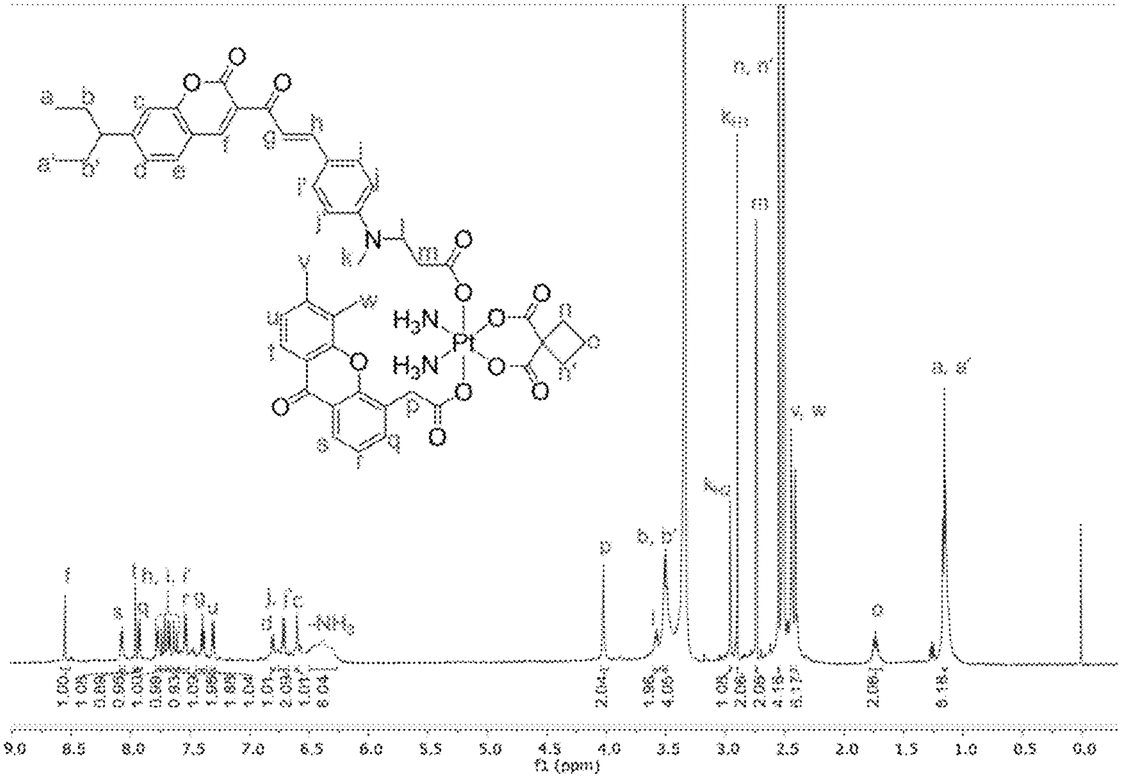
FIG. 16 shows a $^1$H NMR of complex 6 in DMSO-d6.

FIG. 16 shows a $^1H$ NMR of complex 6 in DMSO-d6. $^1H$ NMR (600 MHz, DMSO-d6) δ (ppm): 8.55 (s, 1H), 8.07 (dt, J=8.4, 2.7 Hz, 1H), 7.96 (s, 1H), 7.93 (d, J=8.1 Hz, 1H), 7.77 (dd, J=7.4, 1.8 Hz, 1H), 7.73 (d, J=15.5 Hz, 1H), 7.68 (d, J=9.0 Hz, 1H), 7.62 (d, J=15.5 Hz, 0H), 7.54 (d, J=8.7 Hz, 2H), 7.39 (t, J=7.6 Hz, 1H), 7.31 (d, J=8.2 Hz, 1H), 6.81 (dd, J=9.1, 2.4 Hz, 1H), 6.71 (d, J=9.0 Hz, 2H), 6.60 (d, J=2.4 Hz, 1H), 6.39 (s, 6H), 4.03 (s, 2H), 3.58 (t, J=7.4 Hz, 2H), 3.52-3.49 (m, 4H), 2.96 (s, 1H), 2.90 (s, 2H), 2.74 (s, 2H), 2.55 (s, 4H), 2.45-2.40 (m, 6H), 1.74 (p, J=8.2 Hz, 2H), 1.16 (dd, J=8.3, 5.6 Hz, 6H).

Figure 17:
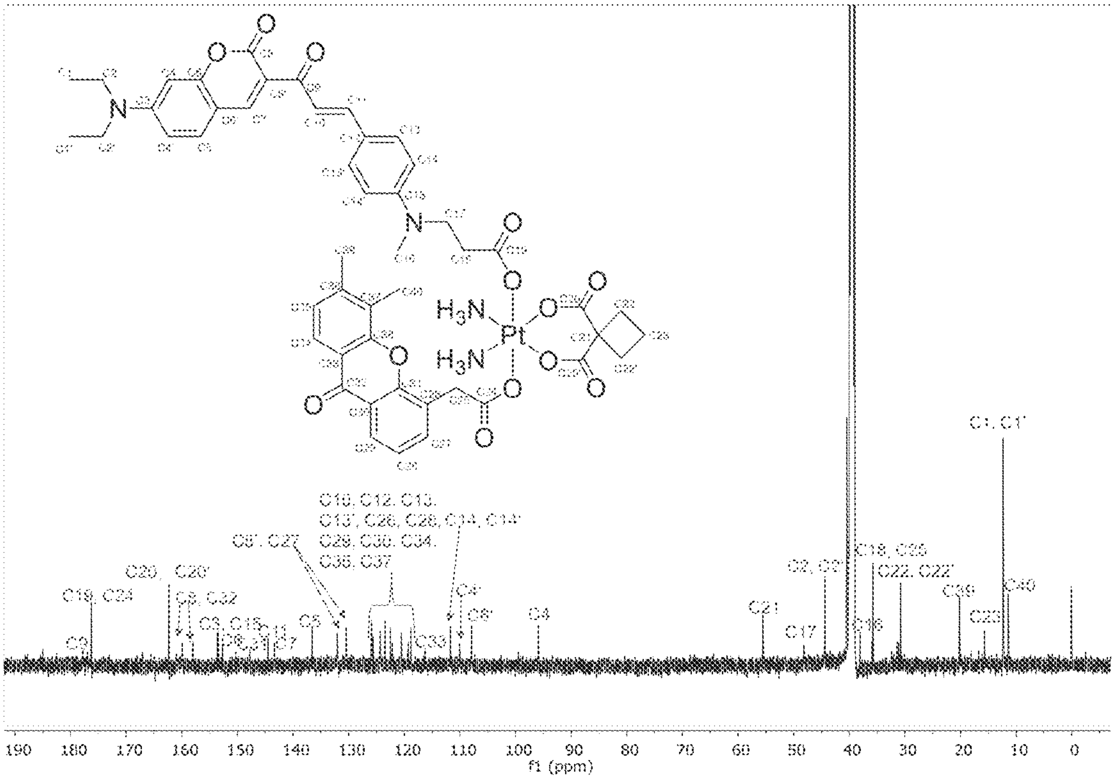
FIG. 17 shows a $^{13}$C NMR analysis of complex 6 in DMSO-d6.

FIG. 17 shows a $^{13}C$ NMR analysis of complex 6 in DMSO-d6. $^{13}C$ NMR (151 MHz, DMSO) δ(ppm): 0.09, 11.45, 12.36, 15.68, 20.21, 30.76, 31.13, 31.39, 35.77, 35.90, 38.06, 44.40, 48.16, 55.56, 95.87, 107.88, 110.04, 111.73, 116.26, 118.78, 119.25, 120.53, 122.15, 122.49, 123.47, 124.29, 125.62, 125.84, 125.93, 130.43, 132.06, 136.57, 143.34, 144.52, 152.69, 153.44, 153.58, 157.99, 159.95, 162.29, 176.23, 176.29.

Figure 18:
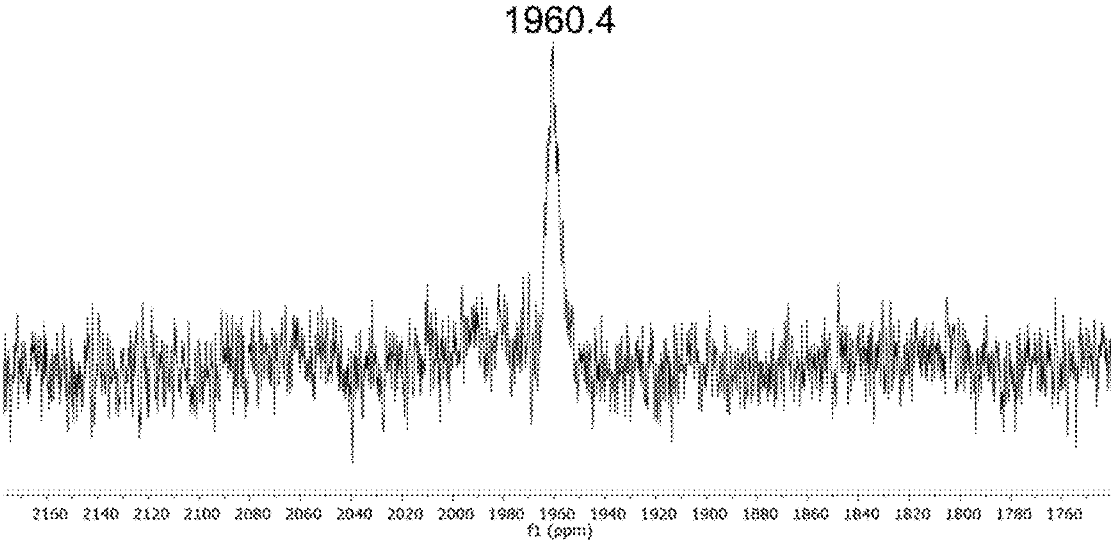
FIG. 18 shows a $^{195}$Pt NMR analysis of complex 6 in DMSO-d6.

FIG. 18 shows a $^{195}Pt$ NMR analysis of complex 6 in DMSO-d6. $^{195}Pt$ NMR (129 MHz, DMSO) δ(ppm): 1960.40.

Figure 19A:
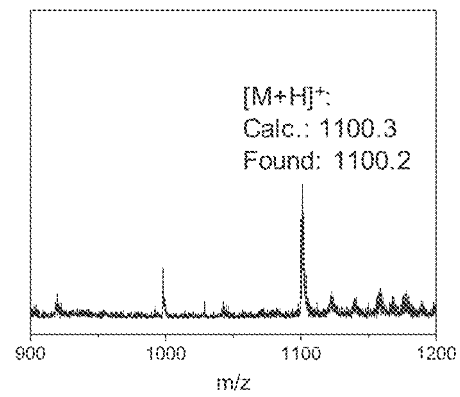
FIG. 19A shows an ESI-MS analysis of complex 6.
Figure 19B:
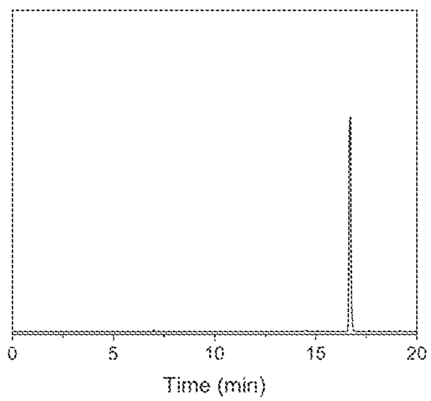
FIG. 19B shows an HPLC chromatograph of complex 6.

FIG. 19A shows an ESI-MS analysis of complex 6 (m/z): $[M+H]^+$ calculated for $C_{49}H_{52}N_4O_{13}Pt$: 1100.3, found: 1100.2. FIG. 19B shows an HPLC chromatograph of complex 6.

Synthesis of complex 7 (i.e., Formula II(b)) in FIG. 2: Complex 5 (i.e., Formula II(a); 860 mg, 1 mmol) and vadimezan (DMXAA, 304 mg, 1.1 mmol) are mixed in 5 mL DMSO, TBTU (48.2 mg, 0.15 mmol) and triethylamine (15 mg, 0.15 mmol) are added into the solution to stir at 50° C. for 12 h. After reaction, 5 mL DCM, 5 mL acetone and 35 mL diethyl ether are added to precipitate the crude product. After centrifugation, the crude product is collected and purified by HPLC to give complex 7. Yield: 61%, purity: 95%.

Figure 20:
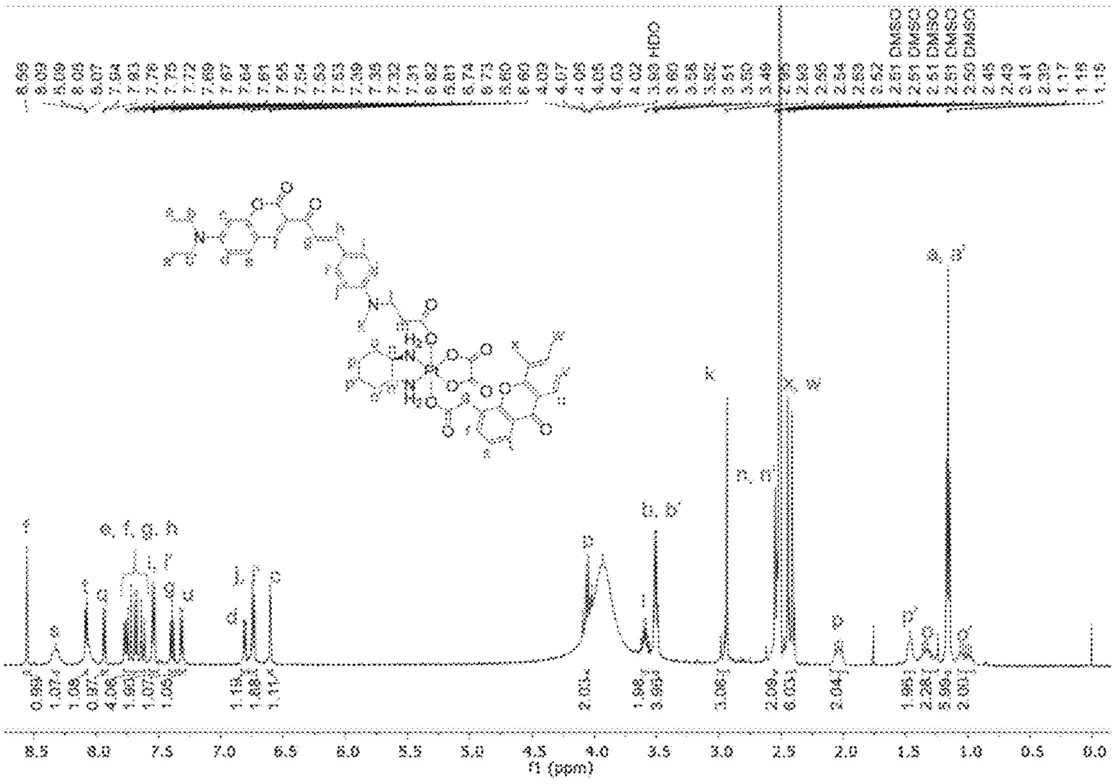
FIG. 20 shows a $^1$H NMR analysis of complex 7 in DMSO-d6.

FIG. 20 shows a $^1H$ NMR analysis of complex 7 in DMSO-d6. $^1H$ NMR (600 MHz, DMSO-$d_6$) δ(ppm): 8.56 (s, 1H), 8.33 (s, 2H), 8.08 (dd, J=8.0, 1.8 Hz, 1H), 8.07 (s, 3H), 7.93 (d, J=8.1 Hz, 1H), 7.79-7.70 (m, 2H), 7.70-7.59 (m, 2H), 7.57-7.51 (m, 2H), 7.39 (q, J=7.3 Hz, 1H), 7.31 (d, J=8.2 Hz, 1H), 6.81 (dd, J=9.1, 2.4 Hz, 1H), 6.78-6.71 (m, 2H), 6.60 (d, J=2.4 Hz, 1H), 4.06 (d, J=10.1 Hz, 1H), 3.59 (h, J=7.5 Hz, 1H), 3.51 (q, J=7.1 Hz, 5H), 2.93 (s, 2H), 2.56-2.51 (m, 4H), 2.46-2.38 (m, 7H), 2.08-2.00 (m, 2H), 1.46 (s, 2H), 1.32 (dt, J=22.2, 10.6 Hz, 1H), 1.16 (t, J=7.1 Hz, 7H), 1.08-0.96 (m, 1H).

Figure 21:
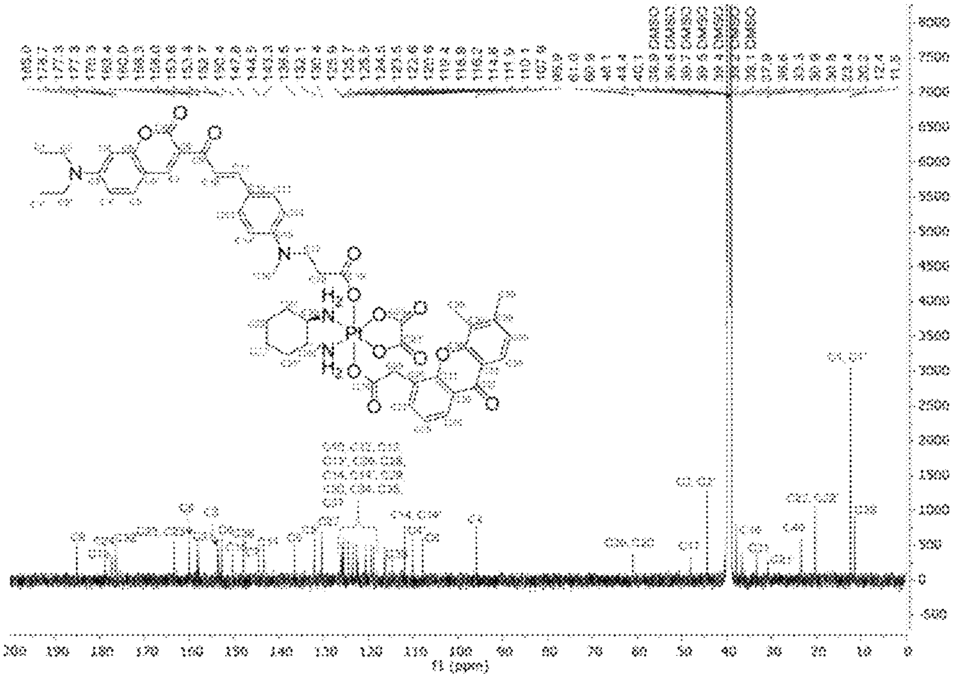
FIG. 21 shows a $^{13}$C NMR analysis of complex 7 in DMSO-d6.

FIG. 21 shows a $^{13}C$ NMR analysis of complex 7 in DMSO-d6. $^{13}C$ NMR (151 MHz, DMSO) δ(ppm): 11.50, 12.36, 20.22, 23.44, 30.84, 30.91, 32.33, 33.10, 33.27, 36.63, 37.88, 44.40, 48.12, 60.86, 61.04, 95.87, 107.89, 110.06, 111.91, 114.62, 116.23, 118.87, 119.35, 120.63, 122.57, 123.52, 124.46, 125.45, 125.70, 125.95, 130.40, 132.08, 136.45, 143.27, 144.51, 147.80, 150.39, 152.70, 153.44, 153.64, 158.00, 158.27, 159.95, 163.37, 176.30, 177.33, 177.35, 178.69, 178.95, 184.98.

Figure 22:
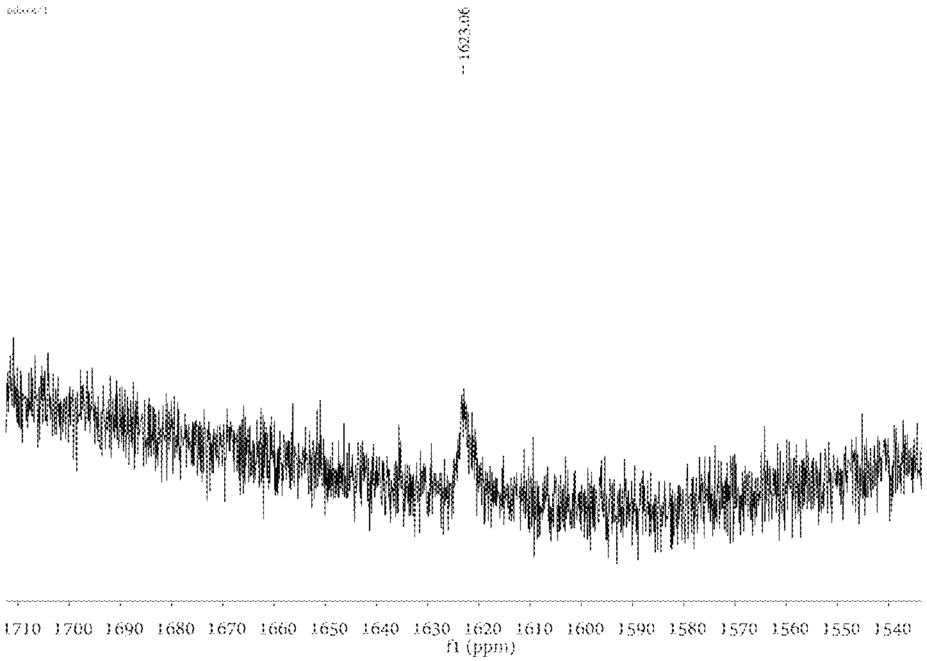
FIG. 22 shows a $^{195}$Pt NMR analysis of complex 7 in DMSO-d6.

FIG. 22 shows a $^{195}Pt$ NMR analysis of complex 7 in DMSO-d6. $^{195}Pt$ NMR (129 MHz, DMSO) δ(ppm): 1623.06. ESI-MS (m/z): $[M+Na]^+$ calculated for $C_{51}H_{54}N_4O_{13}Pt$: 1149.0, found: 1149.1.

FIG. 23A shows an ESI-MS analysis of complex 7, while FIG. 23B shows an HPLC chromatograph of complex 7.

Example 3

The stability and photo-induced reduction of complex 4, complex 5, complex 6 and complex 7 are tested. To test the stability of the complexes in the dark, PBS buffer (10 mM $Na_2HPO_4$, $KH_2PO_4$, 137 mM NaCl, 2.7 mM KCl, pH=7.4) at the final concentration of 10 μM complex with or without ascorbate (2 mM) is incubated in a shaker at 37° C. HPLC analysis is performed at a pre-defined time.

The results are shown in FIG. 24. FIG. 24A shows a RP-HPLC (254 nm) chromatogram of complex 4 (10 μM), FIG. 24B shows a RP-HPLC (254 nm) chromatogram of complex 5 (10 PM), FIG. 24C shows a RP-HPLC (254 nm) chromatogram of complex 6 (10 μM), and FIG. 24D shows a RP-HPLC (254 nm) chromatogram of complex 7 (10 μM). All tests shown in FIGS. 24A-24D are conducted in PBS buffer with the presence of 2 mM ascorbate at different time points.

A photo-induced reduction test is conducted where complexes were dissolved in PBS buffer (10 mM $Na_2HPO_4$, $KH_2PO_4$, 137 mM NaCl, 2.7 mM KCl, pH=7.4) at the final concentration of 10 μM with or without the presence of 2 mM ascorbate and incubated at 37° C. The solution was irradiated with 880 nm laser (0.4 $W/cm^2$) for 20, 40, 60, or 80 min and immediately analyzed by HPLC.

The results are shown in FIGS. 25A-25D. FIG. 25A shows a RP-HPLC (254 nm) chromatograms of complex 4 (10 μM), FIG. 25B shows a RP-HPLC (254 nm) chromatograms of complex 5 (10 μM), FIG. 25C shows a RP-HPLC (254 nm) chromatograms of complex 6 (10 μM), and FIG. 25D shows a RP-HPLC (254 nm) chromatograms of complex 7 (10 μM) in PBS buffer with the presence of 2 mM ascorbate. The solution is irradiated with 880 nm laser; or a continuous laser, (0.4 $W/cm^2$). [1]peak corresponds to platinum(II) drug; [2]peak corresponds to ligand 3; and [3]peak corresponds to DMXAA.

with 10% FBS, 1% NEAA, 1% L-Glutamine, 1% sodium pyruvate, and 100 g/mL penicillin/streptomycin. For A2780cisR and A549cisR cells, 2 μM of cisplatin is added into the culture medium after the attachment to maintain the resistance. All the cells are cultured at 37° C. in 5% $CO_2$.

The cytotoxic profiles of the various complexes against selected cell lines are obtained by a 3-(4,5-Dimethylthiazol-2-yl)-2,5-diphenyltetrazolium bromide (MTT) assay. Cells are seeded into 96-well plates at a density of 2,500 cells per well (for A549, and A2780) or 5,000 cells per well (for A549cisR, A2780cisR, and MRC-5) and incubated for 24 h. Cells are then treated with medium containing various concentrations of complexes for 6 h. The medium is replaced by phenol-red free medium. Then cells are irradiated with near-infrared radiation (880 nm, 0.4 $W/cm^2$) for 80 min. After irradiation, cells are further incubated in fresh medium for 18 h at 37° C. Then, the culture medium is removed, cells are then incubated with FBS free medium containing 1 mg/mL MTT for 2 h. Medium containing MTT is removed and 150 μL DMSO is added to each well. The absorbance is measured at 570 and 630 nm.

The cytotoxicity of oxaliplatin, ligand 3, complex 4, and complex 5 against various cancer cell lines is shown in Table 1. Cells are treated with the indicated complex for 6 h, the culture medium is replaced with fresh medium and irradiated with or without blue light for 1 h. Then cells are cultured for another 42 h.

TABLE 1

| | showing $IC_{50}$ (μM) | | | | | | |
|---|---|---|---|---|---|---|---|
| Cell line | Ligand 3 | Carboplatin | Complex 4 | Complex 6 | Oxaliplatin | Complex 5 | Complex 7 |
| A2780* | 145.7 ± 8.8 | 302.8 ± 34.8 | >50 | >50 | 86.5 ± 7.7 | >50 | >50 |
| A2780* | 57.8 ± 4.4 | 335.9 ± 43.8 | 10.7 ± 2.2 | 11.4 ± 1.5 | 73.7 ± 5.9 | 15.6 ± 2.5 | 5.4 ± 0.9 |
| A2780cisR* | 122.8 ± 9.2 | 667.5 ± 51.1 | >50 | >50 | 249.6 ± 12.6 | >50 | >50 |
| A2780cisR** | 48.5 ± 7.7 | 629.7 ± 43.2 | 11.2 ± 2.8 | 12.7 ± 1.9 | 253.7 ± 18.2 | 19.4 ± 4.5 | 3.6 ± 0.4 |
| A549* | 182.6 ± 9.7 | 417.8 ± 33.6 | >50 | >50 | 97.2 ± 7.5 | >50 | >50 |
| A549** | 59.4 ± 4.1 | 435.2 ± 42.9 | 17.7 ± 5.1 | 11.6 ± 1.2 | 104.3 ± 8.2 | 29.7 ± 3.8 | 5.7 ± 1.4 |
| A549cisR* | 177.3 ± 9.1 | >700 | >50 | >50 | 257.8 ± 11.6 | >50 | >50 |
| A549cisR** | 72.2 ± 5.4 | >700 | 18.9 ± 4.3 | 12.6 ± 2.1 | 269.4 ± 16.3 | 26.9 ± 3.2 | 6.2 ± 1.1 |
| MRC-5* | 193.6 ± 14.8 | 689.6 ± 38.5 | >50 | >50 | 213.4 ± 16.4 | >50 | >50 |

*indicates the test is conducted in the dark with no irradiation.
**indicates the test is conducted with irradiation.

FIG. 26A shows the percentage of complex 4 (10 μM) remaining after irradiation and without irradiation. FIG. 26B shows the percentage of complex 5 (10 μM) remaining after irradiation and without irradiation. FIG. 26C shows the percentage of complex 6 (10 μM) remaining after irradiation and without irradiation. FIG. 26D shows the percentage of complex 7 (10 μM) remaining after irradiation and without irradiation. All tests in FIGS. 26A-26D were run in the PBS buffer (pH 7.4) containing 2 mM sodium ascorbate in the dark or with 880 nm laser irradiation (0.4 $W/cm^2$).

Example 4

Cytotoxicity Test:

Human lung carcinoma A549 cells (American Type Culture Collection, ATCC), and cisplatin-resistant A549cisR cells (American Type Culture Collection, ATCC) are cultured in DMEM with 10% FBS and 100 g/mL penicillin/streptomycin. Human ovarian carcinoma A2780 and cisplatin-resistant A2780cisR cells are cultured in RPMI-1640 with 10% FBS, 1% L-Glutamine, and 100 g/mL penicillin/streptomycin. Human lung fibroblast MRC-5 cells (American Type Culture Collection, ATCC) are cultured in MEM

Example 5

Antibacterial Test:

Growth medium: Lysogeny broth (LB, Invitrogen) is prepared by dissolving 3.0 g of LB powder in 300 mL of MilliQ water. The LB solution is then autoclaved for 45 minutes at 121° C. and allowed to cool prior to addition of antibiotics.

Bacteria are cultured in the LB medium. Before the experiment, the bacteria containing LB stock solution is diluted with fresh LB medium until the $OD_{600}$ of the medium reaches 0.005. Then 200 μL of diluted solution is transferred to a sterile 96-well plate. Complexes at the designed concentration are added and the plates are cultured at 37° C., rotating at 250 rpm, in an incubation shaker. After 2 h, the plates are taken out to irradiate either with or without white light (400-760 nm, 4 $mW/cm^2$) for 10 min, and cultured for another 22 h. Afterwards, 100 μL of the bacterial solution is transferred to a new 96 well plate. The absorption at 600 nm is recorded by a microplate reader (Biotek Powerwave xs Microplate Reader). 100% viability is defined as the $OD_{600}$ value of the untreated group, 0% viability is defined as the medium blank.

FIGS. 27A-27E show the viability of *Escherichia coli* (DH5-α) after different treatments. Bacteria were treated with the indicated compounds for 2 hours, then irradiated with white light (400-760 nm, 4 mW/$cm^2$) for 10 min. Finally, the bacteria were cultured for another 22 hours. FIG. 27A shows a graph with the results for Oxaliplatin, FIG. 27B shows a graph with the results for Carboplatin, FIG. 27C shows a graph with the results for compound 3, FIG. 27D shows a graph with the results for Complex 6, and FIG. 27E shows a graph with the results for complex 7.

FIGS. 28A-28E show the viability of *Staphylococcus aureus* (American Type Culture Collection, ATCC) after different treatments. Bacteria were treated with the indicated compounds for 2 hours, then irradiated with white light (400-760 nm, 4 mW/$cm^2$) for 10 min. Finally, the bacteria were cultured for another 22 hours. FIG. 28A shows a graph with the results for Oxaliplatin, FIG. 28B shows a graph with the results for Carboplatin, FIG. 28C shows a graph with the results for compound 3, FIG. 28D shows a graph with the results for Complex 6, and FIG. 28E shows a graph with the results for complex 7.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

All references specifically cited herein are hereby incorporated by reference in their entireties. However, the citation or incorporation of such a reference is not necessarily an admission as to its appropriateness, citability, and/or availability as prior art to/against the present invention.

What is claimed is:

1. A platinum(IV) complex selected from a group consisting of

Formula II(a)

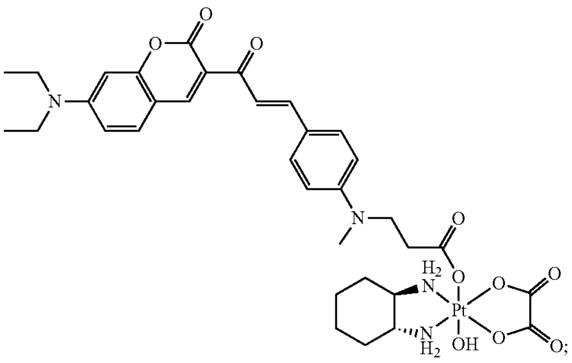

-continued

Formula II(b)

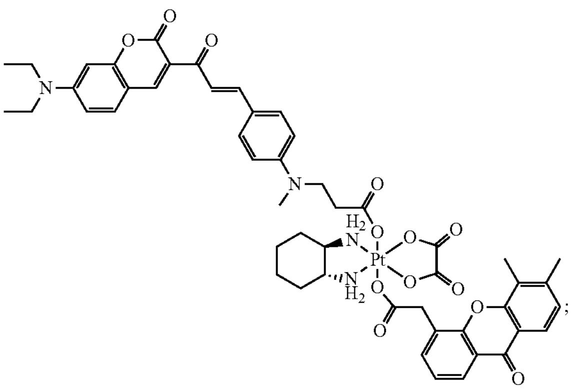

Formula II(c)

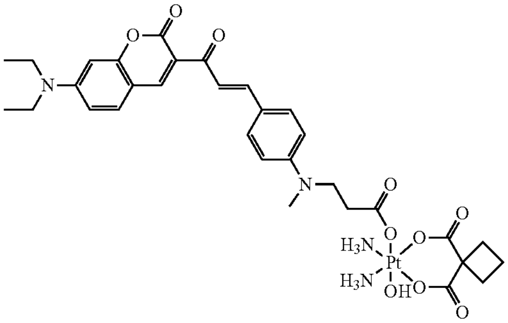

; and

Formula II(d)

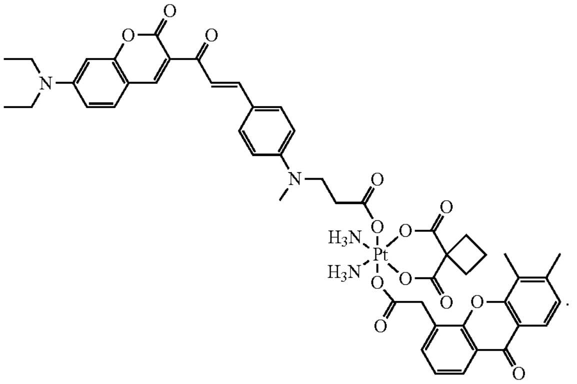

2. A method for manufacturing the platinum(IV) complex of Formula II(a) of claim 1, comprising the steps of:

A) providing c,c,t-[Pt(DACH)$(OH)_2$(ox)];

B) providing a NHS ester of 3-((4-(3-(7-(diethylamino)-2-oxochroman-3-yl)-3-oxoprop-1-en-1-yl)phenyl)(methyl)amino)propanoic acid; and C) reacting c,c,t-[Pt(DACH)$(OH)_2$(ox)] with the NHS ester of 3-((4-(3-(7-(diethylamino)-2-oxochroman-3-yl)-3-oxoprop-1-en-1-yl)phenyl)(methyl)amino)propanoic acid to form the platinum(IV) complex of Formula II(a).

3. A method for manufacturing the platinum(IV) complex of Formula II(b) of claim 1, comprising the steps of:

A) providing a platinum(IV) complex of Formula II(a);

B) providing an NHS ester of 5,6-dimethylxanthenone-4-acetic acid; and

C) reacting the platinum(IV) complex of Formula II(a) with the NHS ester of 5,6-dimethylxanthenone-4-acetic acid to form the platinum(IV) complex of Formula II(b).

4. A method for manufacturing the platinum(IV) complex of Formula II(c) of claim 1, comprising the steps of:

A) providing diammine (cyclobutane-1,1 dicarboxylato) dihydroxido platinum(IV);

B) providing a NHS ester of 3-((4-(3-(7-(diethylamino)-2-oxochroman-3-yl)-3-oxoprop-1-en-1-yl)phenyl)(methyl)amino)propanoic acid;

C) reacting diammine (cyclobutane-1,1 dicarboxylato) dihydroxido platinum(IV) with the NHS ester of 3-((4-(3-(7-(diethylamino)-2-oxochroman-3-yl)-3-oxoprop-1-en-1-yl)phenyl)(methyl)amino)propanoic acid to form the platinum(IV) complex of Formula II(c).

5. A method for manufacturing the platinum(IV) complex of Formula II(d) of claim 1, comprising the steps of:

A) providing the platinum(IV) complex of Formula II(c);

B) providing an NHS ester of 5,6-dimethylxanthenone-4-acetic acid; and

C) reacting the platinum(IV) complex of Formula II(c) with the NHS ester of 5,6-dimethylxanthenone-4-acetic acid to form the platinum(IV) complex of Formula II(d).

6. A pharmaceutical composition comprising a platinum (IV) complex according to claim 1 and a pharmaceutical-acceptable ingredient.

7. The pharmaceutical composition according to claim 6, wherein the pharmaceutical-acceptable ingredient is selected from a group consisting of an additional anti-cancer agent, an adjuvant, an antibody, a binder, a buffer, a diluent, a filler, a pharmaceutically-acceptable carrier, a preservative, a surfactant, a contrast media, a radioactive agent, a photodynamic therapy agent, a photothermal therapy agent, an ultrasonic therapy agent, and a combination thereof.

* * * * *